United States Patent
Geysen et al.

(12)

(10) Patent No.: US 10,005,826 B2
(45) Date of Patent: *Jun. 26, 2018

(54) COMPOUNDS THAT BIND TO THE ERYTHROPOIETIN RECEPTOR

(71) Applicant: EpoDose LLC, Charlottesville, VA (US)

(72) Inventors: Hendrik Mario Geysen, Charlottesville, VA (US); Cyrille V. Gineste, Harrisonburg, VA (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/235,321

(22) Filed: Aug. 12, 2016

(65) Prior Publication Data

US 2017/0029481 A1 Feb. 2, 2017

Related U.S. Application Data

(63) Continuation of application No. 14/118,471, filed as application No. PCT/US2012/037450 on May 11, 2012, now Pat. No. 9,422,338.

(60) Provisional application No. 61/487,747, filed on May 19, 2011, provisional application No. 61/487,752, filed on May 19, 2011, provisional application No. 61/487,760, filed on May 19, 2011, provisional application No. 61/487,771, filed on May 19, 2011.

(51) Int. Cl.
| | |
|---|---|
| *C07K 14/505* | (2006.01) |
| *A61K 38/18* | (2006.01) |
| *A61K 38/12* | (2006.01) |
| *C07K 7/64* | (2006.01) |
| *A61K 47/60* | (2017.01) |
| *A61K 38/00* | (2006.01) |

(52) U.S. Cl.
CPC ............ *C07K 14/505* (2013.01); *A61K 38/12* (2013.01); *A61K 38/1816* (2013.01); *A61K 47/60* (2017.08); *C07K 7/64* (2013.01); *A61K 38/00* (2013.01); *C07K 2319/00* (2013.01)

(58) Field of Classification Search
CPC ................................................ A61K 38/1816
See application file for complete search history.

(56) References Cited

U.S. PATENT DOCUMENTS

| 2006/0040858 A1 | 2/2006 | Holmes et al. |
| 2006/0270831 A1 | 11/2006 | Balu |
| 2008/0081783 A1 | 4/2008 | Duliege |
| 2009/0048147 A1 | 2/2009 | Holmes et al. |
| 2009/0118195 A1 | 5/2009 | Frank et al. |
| 2010/0323949 A1 | 12/2010 | Lu et al. |

FOREIGN PATENT DOCUMENTS

| EP | 2233504 A1 | 9/2010 |
| WO | 0138342 A2 | 5/2001 |
| WO | 2004101606 A2 | 11/2004 |
| WO | 2005040202 A2 | 5/2005 |
| WO | 2009025957 A1 | 2/2009 |

OTHER PUBLICATIONS

International Union of Pure and Applied Chemistry and International Union of Biochemistry, "A One-letter Notation for Amino Acid Sequences (Definitive Rules)", 1971, pp. 639-645.
Hodgkin, "The Structure of Insulin," Diabetes, 1972, pp. 1131-1150.
Bullesbach et al., "Structural Contribution of the A-chain Loop in Relaxin," International Journal of Peptide and Protein Research, 1995, pp. 238-243.
Cernaro et al., "Relaxin: New Pathphysiological Aspects and Pharmacological Properties for an Old Protein," Medicinal Research Reviews, 2013, pp. 1-29.
AstraZeneca Pharmaceuticals LP, "Byetta", 2015, pp. 1-23.
Calceti et al., "Development and in vivo evaluation of an oral insulin-PEG delivery system," European Journal of Pharmaceutical Sciences, 2004, pp. 315-323.
Brange et al., "Chapter 11: Insulin Structure and Stability," Stability and Characterization of Protein and Peptide Drugs: Case Histories; edited by Wang et al., 1993, pp. 315-350.
Moll et al., "A biological stabilization technology for peptide drugs: enzymatic introduction of thioether-bridges," Drug Discovery Today: Technologies, Non Protein Therapeutics, 1999, pp. e13-e18.
Barbieri et al., "New aspects of the insulin resistance syndrome: impact on haematological parameters," Diabetologia, 2001, pp. 1232-1237.

*Primary Examiner* — Lianko G Garyu
(74) *Attorney, Agent, or Firm* — Florek & Endres PLLC

(57) ABSTRACT

The present invention provides mimetics of erythropoietin that bind to the erythropoietin receptor and that are suitable for use in pharmaceutical compositions. The present invention also provides methods of treatment using the mimetics of erythropoietin as well as methods of making the mimetics of erythropoietin.

16 Claims, 13 Drawing Sheets

SEQUENCE LISTING

<160> NUMBER OF SEQ ID NOS: 25

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Met Gly Trp Val
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Beta-Ala

<400> SEQUENCE: 2

Arg Met Ala Trp Val
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Met Phe Trp Val
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: HomoPhe

<400> SEQUENCE: 4

Arg Met Phe Trp Val
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Met Leu Trp Val
1               5

```
<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: NorLeu

<400> SEQUENCE: 6

Arg Met Leu Trp Val
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Met Pro Trp Val
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Met Pro Trp Val
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Nal

<400> SEQUENCE: 9

Arg Met Pro Ala Val
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Nal

<400> SEQUENCE: 10
```

```
His Met Pro Ala Val
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Trp or 2-Nal

<400> SEQUENCE: 11

Arg Met Pro Xaa Val
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: This sequence may encompass 1-5 residues
      wherein some positions may be absent

<400> SEQUENCE: 12

Gly Gly Gly Gly Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Met Gly Pro Ile Thr Trp Val
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: HomoLeu

<400> SEQUENCE: 14

Arg Met Leu Trp Val
1               5

<210> SEQ ID NO 15
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Trp or 2-Nal

<400> SEQUENCE: 15

His Met Pro Xaa Val
1               5

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Asn Tyr Leu Cys Arg Met Gly Pro Ile Thr Trp Val Cys Lys
1               5                   10                  15

Pro Gln Gly Gly
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: 1-Nal

<400> SEQUENCE: 17

Gly Gly Leu Tyr Ala Cys His Met Gly Pro Ile Thr Ala Val Cys Gln
1               5                   10                  15

Pro Gln Gly Gly
            20

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Tyr Leu Cys Arg Met Gly Pro Ile Thr Trp Val Cys Lys Pro
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: 1-Nal

<400> SEQUENCE: 19

```
Leu Tyr Ala Cys His Met Gly Pro Ile Thr Ala Val Cys Gln Pro
1               5                   10                  15
```

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: 1-Nal

<400> SEQUENCE: 20

```
Leu Tyr Ala Cys His Met Gly Pro Ile Thr Ala Val Cys Gln
1               5                   10
```

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: 1-Nal

<400> SEQUENCE: 21

```
Leu Tyr Ala Cys His Met Gly Pro Ile Thr Ala Val Cys
1               5                   10
```

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 1-Nal

<400> SEQUENCE: 22

```
His Met Gly Pro Ile Thr Ala Val
1               5
```

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: 1-Nal

<400> SEQUENCE: 23

```
Arg Met Gly Pro Ile Thr Ala Val
1               5
```

<210> SEQ ID NO 24
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 2-Nal

<400> SEQUENCE: 24

Arg Met Pro Ala Val
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 2-Nal

<400> SEQUENCE: 25

His Met Pro Ala Val
1               5
```

COMPOUNDS THAT BIND TO THE ERYTHROPOIETIN RECEPTOR

CROSS REFERENCE TO RELATED APPLICATIONS

The present application is a continuation of U.S. patent application Ser. No. 14/118,471, filed on Jan. 28, 2014, which is a U.S. National Stage filing under 35 U.S.C. § 371 of International Application No. PCT/US2012/037450, filed May 11, 2012, which in turn claims priority to Provisional Application No. 61/487,747, filed on May 19, 2011; to Provisional Application No. 61/487,752, filed on May 19, 2011; to Provisional Application No. 61/487,760, filed on May 19, 2011; and to Provisional Application No. 61/487,771, filed on May 19, 2011, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 15 2014, is named 2033-001US_SL.txt and is 6,982 bytes in size.

TECHNICAL FIELD OF THE INVENTION

The present invention relates broadly to erythropoietin ("EPO") mimetics that bind to the erythropoietin receptor ("EPOR") and pharmaceutical compositions thereof. Embodiments of the present invention are useful for stimulating erythropoiesis in patients suffering from a range of diseases and disorders.

BACKGROUND OF THE INVENTION

The glycoprotein erythropoietin ("EPO") has a molecular mass of about 34,000 Daltons and is composed of 165 amino acids. It acts as the primary hormone in the regulation of erythropoiesis, in which cell differentiation and proliferation results in increased red blood cell production. EPO is produced by the kidneys during times of low oxygen levels in the blood. EPO binds to the EPO receptor ("EPOR"), reportedly inducing dimerization of two receptors that initiate a cascade leading to the synthesis of hemoglobin and increased production of mature erythrocytes, and consequently higher oxygen levels in the blood. See, e.g., Graber and Krantz, Ann. Rev. Med. 29, 51-66 (1978).

Recombinant human EPO, sometimes referred to as rhEPO and sold under the brand names EPOGEN® (epoetin alfa) and PROCRIT® (epoetin alfa), is widely used in the treatment of patients suffering from anemia, such as anemia from impaired renal function, cancer chemotherapy, or AZT treatment. These drugs are administered either intravenously or subcutaneously.

Efforts have been made to identify alternative peptide EPOR agonists or binding molecules that would improve upon the activity or characteristics of EPO. Erythropoietin (EPO) and a description of novel peptides that bind to the EPO receptor (EPOR) have been described in U.S. Pat. Nos. 7,084,245; 7,414,105; and 7,459,522, each of which are incorporated herein by reference. An X-ray crystal structure of a peptide agonist complexed with the extracellular domain of the EPO receptor has also been published. See Livnah et al., Science, 273, 1996, 464-471; the crystal structure coordinates are hereby incorporated by reference.

The structure shows a homodimeric complex containing two ligands and two EPOR domains with near perfect $C_2$ symmetry. A hydrogen bond exists between the two Gln18 residue sidechains of the dimer near the C-terminal regions of the ligands. The C-terminal regions project away from the binding site towards solution. Based on the near perfect $C_2$ symmetry of the homodimer complex, it is possible that dimeric EPO analogues with pseudo $C_2/C_2$ symmetry may be favored due to an enhanced entropic component to binding.

Wrighton et al. describe a series of small peptides that might act as mimics of EPO. Science, 273, 458 (1996). The compounds were identified using a phage display library and are represented by a family of 16 amino acid peptides having an intramolecular disulfide bond located between two cysteine residues with eight residues between them. U.S. Pat. No. 7,084,245 describes a group of three peptide dimers that are agonists of EPOR. The peptides each contain intramolecular disulfide linkages, and the peptides were covalently joined by a linker at their carboxy terminus. The phage display technology used to identify these EPOR agonists was based on a NNK codon library that was biased towards certain amino acid residues. Moreover, the number of molecules required for a perfect random library of peptides of 14 residues exceeds the numerical limitations of the phage. In addition, 60% of mRNA nucleotide sequences are estimated to include at least one stop codon in a standard NNK library. Thus, it is clear that the number of known EPOR binding compounds, including EPOR agonists, is limited and new molecules are needed.

Moreover, even the compounds that have been identified have limited stability, thereby making their production and handling more difficult and limiting the ways in which they can be administered and used. For instance, the known EPOR agonists contain peptide sequences having intramolecular disulfide linkages which are thought to be necessary for binding. Unfortunately, these disulfide bonds are unstable and can undergo cleavage in a facile manner depending on the conditions, such as under reducing conditions. In addition, peptides as a class are susceptible to acid hydrolysis and enzymatic degradation by proteases which limits the half-life of the drug in the body and further limits the ways they can be administered. Consequently, new EPOR binding compounds, including EPOR agonists, are needed with increased stability, especially molecules that have more stable intramolecular and intermolecular bonds.

It is also known in the art that a patient's hematocrit (i.e., the amount of red blood cells in whole blood, measured as a percentage of the whole blood) and the change in hematocrit can be monitored using readily available, non-invasive finger cuffs that test for hemoglobin levels (a surrogate for hematocrit. These cuffs are also known as pulse oximeters, and commercially available versions are available both over the counter and as a prescription medical device.

SUMMARY OF INVENTION

It is an object of the present invention to provide a new EPO mimetic that is smaller than EPO while still being at least as therapeutically effective as EPO and other prior art rhEPO. It is an additional object of the present invention to provide a new EPO mimetic that is more stable than prior art rhEPO.

It is another object of the present invention to provide a new EPO mimetic that is less expensive to produce than prior art rhEPO.

It is a further object of the present invention to provide a new EPO mimetic that is suitable for subcutaneous injection and can be self-administered privately by the patient.

It is an additional object of the present invention to provide a new EPO mimetic that has fewer contaminants than prior art rhEPO.

It is yet another object of the present invention to provide a new EPO mimetic that, when administered to a patient, induces less anti-EPO antibodies in vivo than prior art rhEPO.

Additional objectives, advantages and novel features of the invention will be set forth in part in the description which follows, and in part will become apparent to those skilled in the art upon examination of the following, or may be learned by practice of the invention.

The present invention provides erythropoietin receptor agonists (EPO mimetics) capable of binding to, and preferably activating, the EPO receptor. The EPO mimetics of the invention comprise a first peptide chain (Chain A) covalently linked to a second peptide chain (Chain B), where Chain A and Chain B each contain a loop structure that is defined by an intra-chain bridge covalently linked across the loop. Without being bound by theory not expressly recited in a particular claim, the loop structure can make hydrophobic interactions (e.g., hydrophobic contacts) with the EPO receptor when bound thereto.

The EPO mimetics of the present invention may bind to a dimeric human EPO receptor extracellular domain with affinities ($K_i$) of, for example, about 200 nM or less, about 100 nM or less, about 50 nM or less, about 20 nM or less, about 10 nM or less, about 9 nM or less, about 5 nM or less and/or about 1 nM or less. The EPO mimetics of the invention may also have advantages in stability and/or bioavailability over known EPO mimetics.

The present invention is directed in various aspects and embodiments to certain EPO mimetic compounds, compositions (including pharmaceutical compositions) comprising such compounds, methods for preparing such compounds, and methods for using such compounds (including methods for therapeutic or prophylactic treatment of a subject in need thereof, such as a subject suffering from anemia or a subject undergoing another treatment which can lead to anemia).

The EPO mimetic compound of the present invention can be a structural analog and preferably a functional analog of erythropoietin. Compounds having the general structure shown in FIG. 1 are disclosed. The compounds can bind to and activate EPOR, for example, by acting as EPO agonists. The compounds can have a Chain A and a Chain B connected via a linker component. Each Chain can contain a loop structure which can have a sequence of monomers that is cyclized at two connection points, $L_1$ and $L_2$, by a bridge component. Each $L_1$ component can be connected to a $L_3$ component via a mid component sequence of monomers and each $L_2$ component can be connected to an end component sequence of monomers. Mid and tail components can be connected via $L_3$ connection points. $L_3$ connection points can also connect Chain A and Chain B of the novel compounds by a dimerizing linker component. Chain A and Chain B can be the same or different sequences of monomers (e.g., amino acids or their isosteric replacements).

More specifically, the bridge component of each of Chain A and Chain B, which is independently selected, comprises a first end covalently linked to an $L_2$ which is adjacent to an N-terminal of the loop, and a second end covalently linked to an $L_1$ which is adjacent to a C-terminal of the loop. $L_3$ of Chain A may be positioned C-terminal of the loop of Chain A, and the $L_3$ of Chain B may be positioned C-terminal to the loop of Chain B. Each of Chain A and Chain B may comprise an independently selected end portion N-terminal of the loop, the N-terminal end portion having an end covalently linked to linking moiety $L_2$. Each of Chain A and Chain B may further comprise an independently selected mid portion C-terminal of the loop and N-terminal of the linker, the mid portion having a first end covalently linked to linking moiety $L_1$ and a second end covalently linked to linking moiety $L_3$. Each of Chain A and Chain B may further comprise an independently selected end portion C-terminal of the linker, the C-terminal end portion having an end covalently linked to linking moiety $L_3$. Each of Chain A and Chain B may further comprise an independently selected tail portion covalently linked thereto.

BRIEF DESCRIPTION OF THE DRAWINGS

FIG. 2 illustrates exemplary structures containing Chains A and B covalently linked via a linker and comprising: up to six amino acid residues or mimetics thereof in each loop; up to three amino acid residues or mimetics thereof in each N-terminal end; an N-terminal capping moiety, Y; up to three amino acid residues or mimetics thereof in each mid component, and a C-terminal moiety, Z. Various components are covalently connected via $L_1$, $L_2$ and $L_3$ linking moieties.

FIG. 3 shows preparation of a first fragment and/or second fragment, designated as Fragment 1/Fragment 2;

FIG. 4 shows preparation of a third fragment, designated as Fragment 3; and

FIG. 5 shows fragment assembly. Figure discloses SEQ ID NOS 24, 24, and 24, respectively, in order of appearance.

DETAILED DESCRIPTION OF THE PRESENT INVENTION

The present invention provides, in one aspect, EPO mimetic compounds. The EPO mimetic compounds can, in preferred embodiments, be EPOR agonists. The EPO mimetic compounds can be capable of binding to and activating the EPO receptor.

Figure 1:
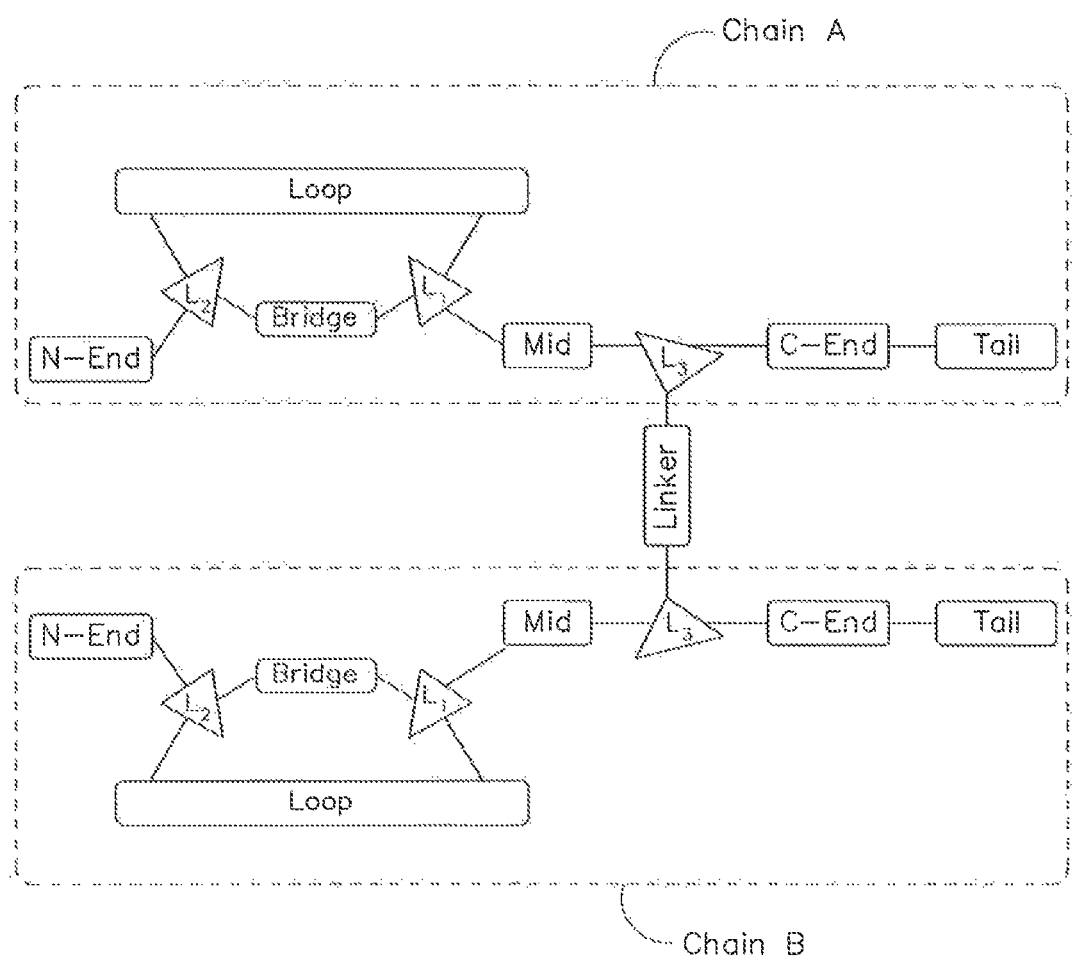
FIG. 1 illustrates a schematic representation of one embodiment of the present invention having a first peptide Chain A and a second peptide Chain B, each comprising a loop and bridge components, and each optionally further comprising mid, N-terminal end, C-terminal end and tail components, Chain A and Chain B being covalently linked via a linker component.
Figure 2:
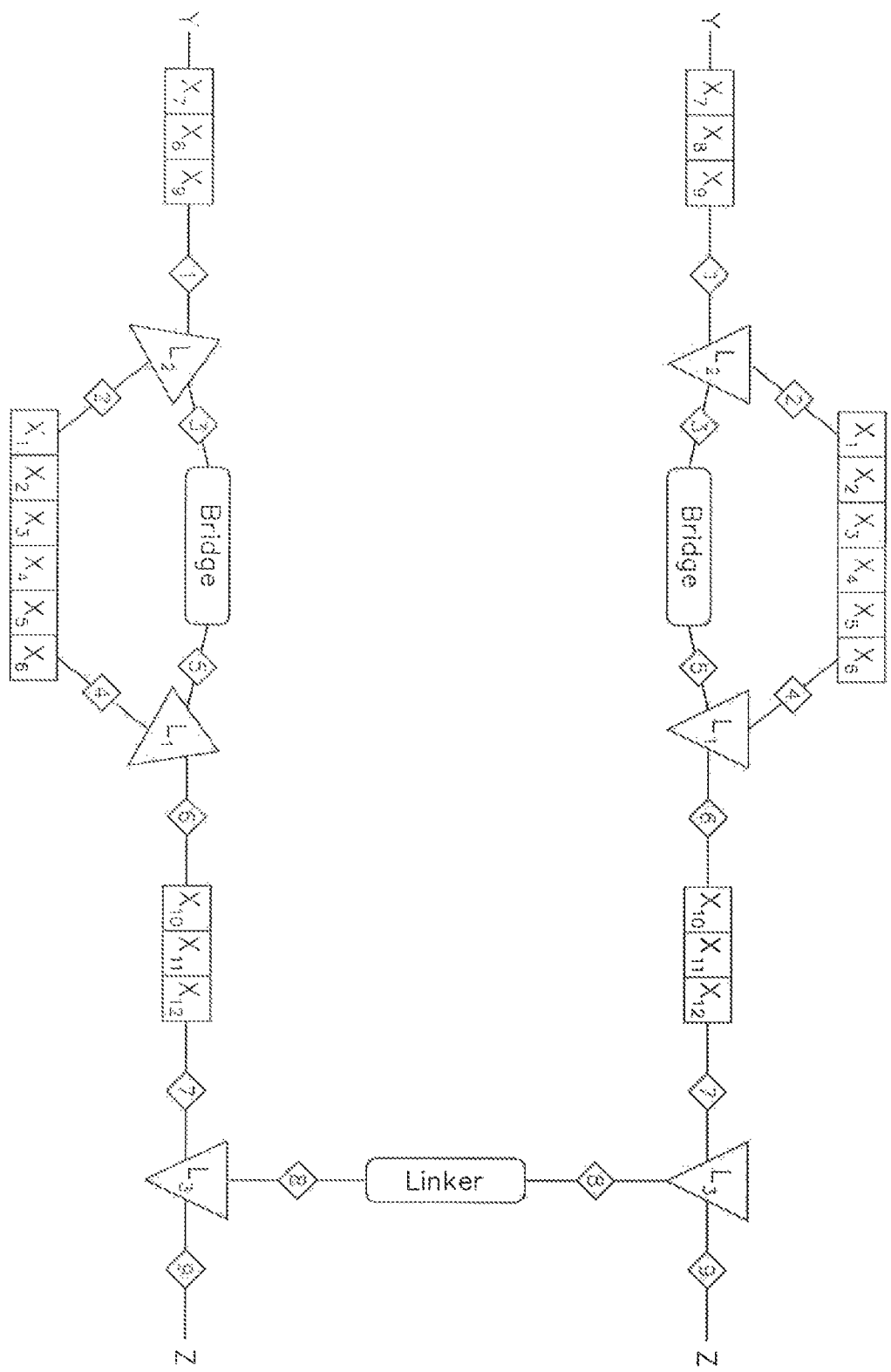
FIG. 2 is a more detailed view of the schematic of FIG. 1.

As shown in FIGS. 1 and 2, the EPO mimetics of the invention comprise a first peptide chain (Chain A) covalently linked to a second peptide chain (Chain B), where Chain A and Chain B each contain a loop. A turn structure of each of the first and second peptide chains (i.e., Chains A and B) can be formed or defined by the loop, taken together with an intrachain bridge covalently linked across the loop. Without being bound by theory not expressly recited in a particular claim, the EPO mimetic compound (and preferably the loop structure of Chain A and/or Chain B) can have hydrophobic interactions with the EPO receptor when bound thereto. The first peptide Chain A can be covalently linked to the second peptide Chain B through at least one interchain linker moiety.

Chain A and/or Chain B can optionally further comprise additional independently selected regions or portions. For example, Chain A and/or Chain B can optionally further comprise an independently selected end portion N-terminal of the loop. The N-terminal end portion can have an end covalently linked to linking moiety $L_2$. Additionally, each of Chain A and or/Chain B can optionally further comprise an independently selected mid portion C-terminal of the loop. In some embodiments, the mid portion can be N-terminal of the interchain linker. Such mid portion can have a first end covalently linked to linking moiety $L_1$ and a second end covalently linked to linking moiety $L_3$. Each of Chain A and/or Chain B can optionally further comprise an independently selected end portion C-terminal of the loop and in some embodiments, C-terminal of the interchain linker. The C-terminal end portion can have an end covalently linked to linking moiety $L_3$. Each of Chain A and/or Chain B can optionally further comprise an independently selected tail portion covalently linked thereto.

It is envisioned that Chain A and Chain B may have the same (or substantially the same) or different amino acid (or mimetics thereof) sequence or structure. In some embodiments, the entire sequence of Chain A and Chain B (or, in fact, any corresponding components thereof, such as the loop structure) may exhibit about 75% or more, 80% or more, 85% or more, 90% or more, or 95% or more sequence identity with each other. Other corresponding components (i.e., N-terminal end regions, mid regions, C-terminal end regions and/or tail regions) may also have these same levels of sequence identity. When Chain A and Chain B have substantially the same sequence, one chain may have, for example, from one to ten, preferably one to five, more preferably one to three and most preferably one or two conserved amino acid substitutions, including conserved substitutions of a non-generically encoded amino acid, and/or one or two isosteric changes in the side chains or peptide backbone, as described herein. In certain embodiments, Chains A and B are the same, at least without regard to any linking or bridge components as discussed elsewhere herein.

Components of Chain A and/or Chain B

Loop

The loop of at least one of Chain A and Chain B, and preferably the loop of each of Chain A and Chain B, comprises at least first and second hydrophobic amino acid residues or mimetics thereof separated by a spacer moiety. The spacer moiety has an absence of hydrogen bonding (e.g., via its backbone) with the extracellular domain of the human EPO receptor when the mimetic is bound thereto. Generally, without wishing to be bound by theory not recited in a particular claim, in this aspect, the spacer moiety does not contain amino acid residues or mimetics thereof that hydrogen bond through atoms included within the backbone chain thereof with the EPO receptor. The length of the loop and/or the composition of the loop may be such that hydrophobic groups in the loop structure are well positioned for interaction with hydrophobic groups of the EPO receptor (e.g., independent of hydrogen bonding).

In some embodiments of the present invention, the loop of at least one of Chain A and Chain B, and preferably the loop of each of Chain A and Chain B, has at least 65% hydrophobic amino acid residues or mimetics thereof, as compared to the total number of amino acid residues or mimetics thereof within the loop. Such composition of the loop structure allows for favorable interaction between hydrophobic groups of the EPOR and hydrophobic components of the loop, to thereby support high affinity binding. In some embodiments of the present invention, the loop of either or both of Chain A and Chain B may independently contain at least 80% (e.g., 4 or 5), at least 83% (e.g., 5 or 6) or 100% hydrophobic amino acid residues or mimetics thereof. At least one or at least two hydrophobic residues may contain aliphatic side chains, such as M, A, I, L or V, or a conservative substitution or isosteric replacement thereof, such as homocysteine, β-alanine, norisoleucine, norleucine or norvaline, respectively. Additional aliphatic amino acid residues include any natural or non-natural amino acid having linear or branched, saturated or unsaturated, substituted or unsubstituted hydrocarbyl chain of from about 2 to about 10 carbon atoms, which substituted hydrocarbyl may include one or more heteroatoms including S, O or N within the main chain.

Alternatively, at least one or at least two hydrophobic residues in the loop may contain aromatic side chains, such as F or W, or a suitable replacement thereof such as homophenylalanine or naphthylalanine (1- or 2-), respectively). Additional aromatic amino acid residues (e.g., as conservative or isosteric substitutions for phenylalanine or tryptophan) include non-genetically encoded amino acids having a substituted or unsubstituted aromatic group covalently linked to the α-carbon, such as by side-chain sub-moieties (e.g., alkyl sub-moieties) comprising about 2 to about 10 carbon atoms in the main portion of the side chain therebetween. Such side-chain sub-moieties may ben any linear or branched, saturated or unsaturated, or substituted or unsubstituted hydrocarbyl chain. While the hydrocarbyl chain is generally hydrophobic in nature, the chain may further comprise one or more heteroatoms including S, O or N within the main chain of the side-chain sub-moiety. The aromatic moiety may be a monocyclic or multicyclic ring system, wherein at least one ring is aromatic, comprising about 6 to about 14 carbon atoms, preferably about 6 to about 10 carbon atoms. Non-limiting examples of suitable aromatic groups include substituted or unsubstituted phenyl, naphthyl, indolyl, indanyl, indenyl, tetrahydronaphthyl, anthracenyl and fluorenyl.

In some embodiments of the present invention, the loop of at least one of Chain A and Chain B, and preferably the loop of each of Chain A and Chain B, comprises at least first and second hydrophobic amino acid residues or mimetics thereof separated by a spacer moiety. Preferably, the spacer moiety is a peptide spacer moiety having a sequence of not more than 3 amino acid residues linked via amide bonds (e.g., peptide bonds). Alternatively, the first and second hydrophobic amino acid residues or mimetics thereof may be separated by a spacer moiety other than a peptide consisting of (i.e., a sequence of) amino acid residues linked by amide bonds. In preferred embodiments, the spacer moiety can be, for example, a hydrocarbyl group or a substituted hydrocarbyl group (other than such a peptide), including a substituted or unsubstituted hydrocarbyl optionally having one or more heteroatoms in the main chain. Without being bound by theory not expressly recited in the claims, the spacer moiety may position the first and second hydrophobic residues for favorable interaction with one or more hydrophobic groups in the receptor binding pocket (e.g., one, two, or each of residues F93, M150, and F205 of the EPOR).

In some preferred embodiments, the loop of at least one of Chain A and Chain B, and preferably the loop of each of Chain A and Chain B, has a sequence of at least about two and not more than about six amino acid residues or mimetics thereof—and preferably five amino acid residues or mimetics thereof—and at least two residues of the sequence are independently selected hydrophobic amino acid residues or mimetics thereof. Preferably, the at least two residues of the sequence are independently selected bulky hydrophobic amino acid residues or mimetics thereof. More preferably, the at least two residues of the sequence are independently selected from the group consisting of M, F, L, I, W, V, naphthylalanine and mimetics thereof. For example, the first hydrophobic residue may be an amino acid residue or mimetic thereof with an aliphatic side chain such as methionine, or mimetic thereof, and the second hydrophobic residue may be an amino acid residue or mimetic thereof with an aromatic side chain such as tryptophan or a mimetic thereof. In such an embodiment, the loop structure of the EPO mimetic is relatively small and hydrophobic in character, and therefore without being bound by theory not expressly recited in the claims, may be well positioned to interact with hydrophobic groups in the EPO binding pocket, when bound to the EPO receptor.

In some embodiments, without being bound by theory not expressly recited in the claims, the loop does not contain amino acid residues or mimetics thereof that hydrogen bond with the EPO receptor without also contributing Van der Waals contacts with the receptor. Thus, amino acid residues or mimetics in the loop that do not contribute hydrophobic contacts with the receptor (e.g., such as residues in the spacer moiety), preferably also do not form hydrogen bonds with the backbone of residue M150 of the EPO receptor (i.e., M150 of one or both subunits of the dimerized EPO receptor), and/or the backbone and/or side chains of T151 or S152 of the EPO receptor (i.e., in one or both subunits of the dimerized EPO receptor). In some such embodiments, carbonyl oxygens or other potential hydrogen bond acceptors, if present in the loop region of the EPO mimetic compound (and particularly if present in the spacer), are positioned so as to minimize or obviate hydrogen bond formation with donor atoms of the EPOR (i.e., with M150, T151 and/or S152 in one or both subunits of the dimerized receptor), without compromising hydrophobic contacts between the loop and the EPOR.

More specifically, and as shown in FIG. 2, the loop structure of Chain A and/or Chain B may comprise a sequence represented by $X_1$-$X_2$-$X_3$-$X_4$-$X_5$-$X_6$ where each X represents an amino acid residue or mimetic thereof. Generally, $X_1$ is optional and (if present) is independently selected between Chain A and/or Chain B to include a basic amino acid residue or mimetic thereof, preferably such as a basic amino acid residue selected from the group consisting of R, K, H and mimetics thereof. $X_2$ is a hydrophobic residue and is preferably independently selected from the group consisting of M, F, L, I, W and mimetics thereof, and more preferably selected from the group consisting of M, F, I and mimetics thereof. $X_3$ and $X_4$ are each independently optional and (if present) can be a spacer moiety, in which at least one of $X_3$ and $X_4$ is independently selected from the group consisting of G, β-alanine, proline, a proline analog, a hydrophobic amino acid residue and mimetics thereof; the other of $X_3$ and $X_4$ (if present) is selected from the group consisting of an amino acid residue and mimetics thereof. $X_5$ may by a hydrophobic residue and is preferably independently selected from the group consisting of W, naphthylalanine (e.g., 1-Nal, 2-Nal), F and mimetics thereof. For example, where $X_5$ is a mimetic of tryptophan, $X_5$ may be an amino acid (or isosteric replacement thereof) carrying a side chain comprising a substituted or unsubstituted indolyl, indenyl, or indanyl group, preferably substituted with one or more linear or branched $C_1$-$C_{20}$ hydrocarbyl groups including alkyl, alkenyl or alkynyl, such as propyl or butyl. $X_6$ is optional and (if present) is independently selected from V, L, I and mimetics thereof. Without being bound by theory not expressly recited in the claims, the binding affinity of the EPO mimetic for the EPO receptor derives at least in part from hydrophobic interactions between the loop structure comprising the sequence $X_1$-$X_2$-$X_3$-$X_4$-$X_5$-$X_6$ and the EPO receptor and, in some cases, between such loop structure and at least one, two or each of F93, M150 and F205 of the EPO receptor. In such embodiments, the EPO mimetic compound can activate the receptor when bound thereto.

In preferred embodiments, $X_1$ is independently selected from the group consisting of R, H and mimetics thereof; $X_2$ is independently selected from the group consisting of M and mimetics thereof; $X_3$ is independently selected from the group consisting of G, P, β-alanine (βA) and mimetics thereof and preferably from the group consisting of G, P and mimetics thereof; $X_4$ is not present; $X_5$ is independently selected from the group consisting of W, naphthylalanine and mimetics thereof; and $X_6$ is independently selected from the group consisting of V and mimetics thereof.

$X_1$ may be at a sequence position in either or both of Chain A and Chain B ranging from 2 to about 18, preferably from 3 to about 12 and more preferably at positions 3, 4, 5 or 6. Such sequence position is generally determined without regard to any N-terminal capping moiety on the Chain A or Chain B.

Exemplary loop sequences according to the present invention include R-M-G-W-V (SEQ ID NO: 1); R-M-βA-W-V (SEQ ID NO: 2); R-M-F-W-V (SEQ ID NO: 3); R-M-homoF-W-V (SEQ ID NO: 4); R-M-L-W-V (SEQ ID NO: 5); R-M-nL-W-V (SEQ ID NO: 6); R-M-P-W-V (SEQ ID NO: 7); H-M-P-W-V (SEQ ID NO: 8); R-M-P-Nal-V (SEQ ID NO: 9); and H-M-P-Nal-V (SEQ ID NO: 10). Another preferred loop sequence is R-M-P-X-V (SEQ ID NO: 11). Wherein R, M, G, W, V, βA, F, homoF, L, nL, P, H and Nal are as defined above and X can be equivalent to W, preferably 2-Nal.

It is envisioned that the loop structure of Chain A and/or Chain B can comprise one or more modifications to the backbone thereof, particularly one or more isosteres as substitutive replacements for a corresponding one or more amide moieties, —C(O)NH—, of the backbone structure of the loop moiety.

Spacer Moiety

The spacer moiety may consist of three or fewer amino acid residues linked by amide (e.g., peptide) bonds. In some embodiments, the spacer moiety may comprise glycine, β-alanine, phenylalanine, homophenylalanine, leucine, norleucine, proline or mimetics thereof, including conservative and/or isosteric substitutions thereof. In some embodiments, the spacer moiety is a β-amino acid residue or mimetic thereof. Alternatively, the spacer moiety may be a non-peptidyl spacer moiety such as a substituted or unsubstituted hydrocarbyl other than a peptide comprising amino acid residues linked by amide bonds, such as substituted or unsubstituted, linear or branched, $C_1$-$C_5$ alkyl, $C_1$-$C_{15}$ alkenyl or $C_1$-$C_{15}$ alkynyl. In some embodiments, the spacer moiety can be a hydrocarbyl substituted or interrupted in the main chain by one or more heteroatoms or functional groups selected from —O—, —N—, —C(O)—, —S— and —P— and combinations thereof; preferably selected from —O—, —N— and —S— and combinations thereof. Exemplary non-peptidyl spacer moieties include (—($CH_2$)$_n$—O—($CH_2$)$_m$—)$_o$, (—($CH_2$)$_n$—N(R)—($CH_2$)$_m$—)$_o$, (—($CH_2$)$_n$—NHC(O)NH—($CH_2$)$_m$—)$_o$, (—($CH_2$)$_n$—NHC(O)O—($CH_2$)$_m$—)$_o$, (—($CH_2$)$_n$—C(O)—($CH_2$)$_m$—)$_o$, (—($CH_2$)$_n$—C(O)O—($CH_2$)$_m$—)$_o$, (—($CH_2$)$_n$—NS(O)$_2$—($CH_2$)$_m$—)$_o$, (—($CH_2$)$_n$—S—($CH_2$)$_m$—)$_o$ and mixtures thereof, wherein n and m are integers from 1 to about 9 and may be the same or different, o is an integer from about 1 to about 5, preferably 1 or 2; and R is H or a substituent. In other embodiments, the spacer moiety may have a length of 11 carbon and/or heteroatoms or less, such as 7, 8, 9, 10 or 11 carbons and/or heteroatoms in the main chain thereof. Thus, in these embodiments, the spacer moiety may have less than about 11, 12 or 13 chemical bonds, e.g., 7, 8, 9, 10 or 11 chemical bonds.

Bridge

The bridge can be any type of bond but is preferably a series of about 3-7 bonds, more preferably about 4-5 bonds and most preferably about 5 bonds. The series of bonds can also be any type of chemical group with preferred groups being ether, disulfide bonds, amides, carbamates, esters, thioesters, polyethers, thioethers, phenolic ethers, amines (e.g., secondary, tertiary or quaternary amines) sulfonamides and carbon-carbon bonds. Ether bonds are especially preferred.

In certain embodiments, the intrachain bridge of Chain A and/or Chain B is or includes a $C_3$-$C_{10}$ hydrocarbon, preferably a $C_3$-$C_7$ hydrocarbon, which may be linear or branched, saturated or unsaturated and substituted or unsubstituted. The intrachain bridge may comprise an alkylene-containing unit or repeating units (e.g., alkylene-moiety-alkylene). For example, the intrachain bridge may comprise a unit represented as (alkylene-O-alkylene), (alkylene-N(R)C(=O)-alkylene), (alkylene-C(=O)N(R)-alkylene), (alkylene-N(R)C(=O)O-alkylene), (alkylene-OC(=O)N(R)-alkylene), alkylene-OC(=O)-alkylene), (alkylene-C(=O)O-alkylene), (alkylene-SC(=O)-alkylene), (alkylene-C(=O)S-alkylene), (alkylene-S-alkylene), (alkylene-N(R)-alkylene), alkylene-N(R)SO$_2$-alkylene), (alkylene-SO$_2$N(R)-alkylene) and (alkylene-C(=O)-alkylene) and combinations thereof, where R is selected from the group consisting of hydrogen or a substituent, such as an optionally substituted and/or unsaturated alkyl, acyl or sulfonyl.

When the intrachain bridge comprises an ether moiety or a polyether moiety, it may be represented as a unit or repeating units of (alkylene-O-alkylene)$_m$, where m is selected from 1 to about 5. Exemplary intrachain bridges in these embodiments have the formula: ($CH_2$)$_n$—O—($CH_2$)$_n$, where n is independently selected from 1 to about 5. For example, an ether-based intrachain bridge may comprise a moiety selected from: —$CH_2$—O—$CH_2CH_2$—, —$CH_2CH_2OCH_2$—, —$CH_2CH_2OCH_2CH_2$—, —$CH_2CH_2CH_2OCH_2CH_2$— and —$CH_2CH_2$—O—$CH_2CH_2CH_2$—.

Linker

Chain A and Chain B may be covalently linked though at least one linker moiety having a structure disclosed herein, and/or having a first end covalently linked to Chain A at a sequence position ranging from about residue 5 to about residue 18 thereof (preferably about residue 11 to about residue 17 and even more preferably about residue 12 or 13), and having a second end covalently linked to Chain B at a sequence position ranging from about residue 5 to about residue 18 thereof (preferably about residue 11 to about residue 17 and even more preferably about residue 12 or 13). For example, the linker may preferably comprise one or more moieties selected from: $C_1$-$C_{10}$ hydrocarbon (linear, branched or cyclic), heterocycle, ether, amide, carbamate, ester, thioester, polyether, thioether, phenolic ether, amine, sulfonamide, ketone and combinations thereof. The moieties may be oriented in either direction, e.g., an amide moiety may be oriented as —N(R)C(=O)— or —C(=O)N(R)—. When the moieties are amide, amine or sulfonamide, the nitrogen may be substituted with a substituent denoted as R; R may be H or a substituent such as a tail as described herein, or optionally substituted and/or unsaturated alkyl, acyl or sulfonyl.

In other embodiments, the linker comprises an optionally substituted alkylene, uninterrupted by the above-listed moieties. The linker may be or may contain a $C_3$-$C_{20}$ hydrocarbon, which may be linear or branched, and which may be substituted or unsubstituted. Alternatively, the hydrocarbon chain may also contain one or more heteroatoms in the main chain, such as —O—, —S— and/or —N—, with the total number of atoms in the main chain being from about 8 to about 20. Thus, the linker may be an alkylene; where the alkylene contains one or more units of unsaturation, the unit(s) may each contain one or two substituents, such as halogen substituents (e.g., independently selected from F, Cl or Br) and may be in trans configuration.

The term "alkylene" as used herein means an optionally substituted $C_1$-$C_{20}$ straight or branched alkyl group and includes, e.g., methylene, ethylene, trimethylene, propylene, tetramethylene, pentamethylene, etc. Optional substituents of the alkylene include, e.g., one or more of the following: halogen, alkyl (optionally substituted and/or unsaturated), cycloalkyl, heterocycloalkyl, alkoxy, hydroxyl, amino, aryl, amido, carbamoyl, thio, carbonyl, carboxy, oxycarbonyl and carboalkoxy. Any substituent may be used so long as it does not interfere with binding to the EPO receptor.

In one embodiment, the linker comprises an alkylene moiety which may be represented as (alkylene-O-alkylene)$_m$, (alkylene-N(R)C(=O)-alkylene)$_m$, (alkylene-C(=O)N(R)-alkylene)$_m$, (alkylene-N(R) C(=O)O-alkylene)$_m$, (alkylene-OC(=O)N(R)-alkylene)$_m$, alkylene-O C(=O)-alkylene)$_m$, (alkylene-C(=O)O-alkylene)$_m$, (alkylene-SC(=O)-alkylene)$_m$, (alkylene-C(=O)S-alkylene)$_m$, (alkylene-S-alkylene)$_m$, (alkylene-N(R)-alkylene)$_m$, alkylene-N(R)SO$_2$-alkylene)$_m$, (alkylene-SO$_2$N(R)-alkylene)$_m$ and (alkylene-C(=O)-alkylene)$_m$ and combinations thereof, where R is hydrogen or a substituent, such as a tail as described herein or an optionally substituted and/or unsaturated alkyl, alcyl or sulfonyl, and where m is selected from 1 to about 5, preferably 1, 2 or 3. Preferred linkers contain a unit or repeating units comprising ether and/or amide moieties, including structures represented as —($CH_2$)$_{2-8}$—O—($CH_2$)$_{2-4}$—O—($CH_2$)$_{2-8}$—, —($CH_2$)$_{2-8}$ N(R)—C(O)—(CH$_2$)$_{2-8}$—, —CH$_{2-8}$—C(=O)N(R)—CH$_2$)$_{2-8}$ and combinations thereof, where R is selected from the group consisting of hydrogen, a tail as described herein and an optionally substituted and/or unsaturated alkyl, acyl or sulfonyl.

In further embodiments, the linker is an ether-based linker having a structure represented by the general formulation alkylene-O-alkylene-O-alkylene, where the alkylene is as defined above. In these embodiments, the alkylene moieties may each independently have a length of from 1 to 5 carbon atoms, preferably 2-3 carbon atoms. The alkylene moieties may each, independently, be optionally substituted (e.g., with substituted or unsubstituted hydrocarbyl, e.g., as a tail). Exemplary covalent linkers in accordance with these embodiments may have structures represented by —(CH$_2$)$_{2-8}$—O—(CH$_2$)$_{2-4}$—O—(CH$_2$)$_{2-8}$— or —(CH$_2$)$_{1-5}$—O—(CH$_2$)$_{1-3}$—CH(R)—O—(CH$_2$)$_{1-5}$—, where R may be H, or any substituent as defined in above (e.g., an amide group or a tail). In these embodiments, the linker preferably has a total of from 10-14 bonds in the main chain, preferably about 11 or about 12 bonds.

Alternatively, the linker may contain a heterocyclic moiety, as represented by Formula I below, wherein each of $Q_1$, $Q_2$, $Q_3$ and $Q_4$ are the same. Especially preferable are symmetrical linkers in which $Q_1$ and $Q_2$ are the same, and $Q_3$ and $Q_4$ are the same. In Formula 1, R may be H or a substituent, such as a tail as described herein.

Formula 1

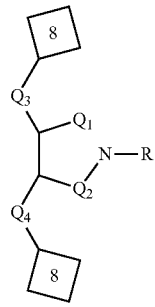

In accordance with these embodiments, the linker may contain a 5-, 7-, 9-, 11- or 13-memembered ring. Exemplary embodiments include the interchain linker moieties as shown in Formulas 1A, 1B and 1C (shown with an optional tail):

Formula 1A

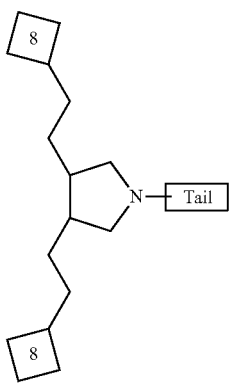

Formula 1B

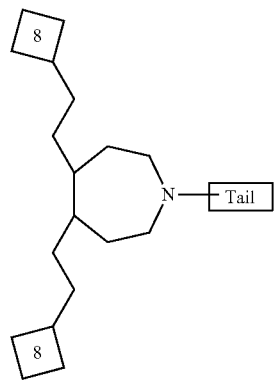

Formula 1C

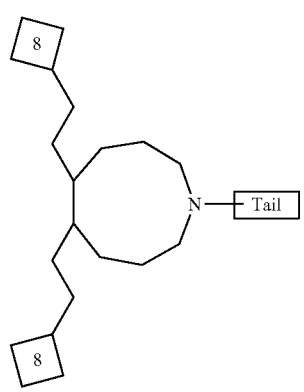

The length of the interchain linking moiety is not tightly constrained and is not narrowly critical. Rather, the linker may have a length equal to from about 8 linear carbon-carbon bonds to about 30 linear carbon-carbon bonds, preferably from about 12 linear carbon-carbon bonds to about 20 linear carbon-carbon bonds.

$L_1$, $L_2$, $L_3$ $L_1$, $L_2$ and/or $L_3$ can be any type of linking moiety with preferred moieties being amino acid residues or mimetics thereof or multifunctional moieties containing functional groups such as ether, amide and carbonyl sufficient to connect and orient the loop, bridge and N-terminal end portion as shown in FIG. 2. In some embodiments, the linking moiety is a cysteine residue or mimetic thereof. In other embodiments, the linking moiety corresponds to or simulates a peptide backbone between the N-terminal portion and the loop.

Mid Portion

The mid portion is a sequence one to five amino acid residues or mimetics thereof, and preferably one, two or three amino acid residues or mimetics thereof. It is also preferred that the mid portion have a basic amino acid, with preferred basic amino acids such as R, K, H or mimetics thereof. Other preferred amino acids include homoarginine, hydroxylysine or methylhistidine. Still other preferred amino acids include proline, proline analogs, or other cyclic amino acid residues or mimetics thereof. Preferred proline analogs may contain 4-, 5-, 6- or 7-membered rings. As shown in FIG. 2, the mid portion can comprise the sequence of $X_{10}$-$X_{11}$-$X_{12}$ where X is an amino acid residue or mimetic thereof. $X_{10}$ may be selected from the group consisting of a basic amino acid residue or mimetic thereof; $X_{11}$ may be a cyclic amino acid residue such as a P, a proline analog, hydroxyproline and mimetics thereof; and $X_{12}$ is a polar amino acid residue or mimetic thereof with Q or N being preferred. The mid portion can also comprise the sequence of $X_{10}$-$X_{11}$ where X is an amino acid residue or mimetic thereof. $X_{10}$ is selected from the group consisting of a basic amino acid residue and mimetics thereof; $X_{11}$ is a cyclic amino acid residue, preferably selected from the group consisting of P, a proline analogue, hydroxyproline and mimetics thereof. Preferred sequences include X-P, where X is a basic or polar amino acid (preferably basic) or mimetic thereof, with R-P, homoR-P and K-P being preferred.

N-Terminal End Portion

The N-terminal end portion is an optional component of a Chain A and/or Chain B. The N-terminal end portion is a sequence of, preferably, one to five amino acids or mimetics thereof, even more preferably one, two, three or four amino acids or mimetics thereof, and most preferably about three amino acids or mimetics thereof. As shown in FIG. 2, the N-terminal end portion can have the general sequence of $X_7$-$X_8$-$X_9$ where X is an amino acid residue or mimetic thereof; $X_7$ may be selected from the group consisting of D, E, N, T and mimetics thereof and in each case may comprise a capping moiety ("Y" in FIG. 2). Alternately, conservative substitutions of amino acid residues or mimetics thereof may be positioned at $X_7$. $X_8$ may be selected from the group consisting of tyrosine and mimetics thereof.

Alternatively, conservative substitutions of amino acid residues or mimetics thereof may be positioned at $X_8$, which may include residues carrying side chains capable of making hydrophobic contacts with the receptor (e.g., hydrophobic packing), and optionally contributing a hydrogen bond. For example, exemplary substitutions at $X_8$ include T, W, V and tyrosine methyl ether, as well as residues having side chains containing hydrophobic groups commensurate in size with that of tyrosine. $X_9$ may be independently selected from the group consisting of S, T, K, L, Y and mimetics thereof. Alternatively, conservative substitutions of amino acid residues or mimetics thereof may be positioned at $X_9$. In some embodiments, the N-terminal end portion comprises the amino acid residue sequence of N-Y-L. If the N-terminal end portion contains only two amino acid residues or mimetics thereof, and optionally a capping moiety, then a first amino acid may be selected from tyrosine and mimetics thereof, and a second amino acid residue or mimetic thereof may be selected from the group consisting of S, T, K, L, Y and mimetics thereof. A preferred sequence is Y-L.

If the N-terminal end portion comprises only one amino acid residue or mimetic thereof, the amino acid residue or mimetic thereof may be selected from the group consisting of S, T, K, L, Y and mimetics thereof; Y and L are preferred. The capping moiety ("Y", in FIG. 2) can be derived from a reaction of an N-terminal amine group with a derivatizing agent known in the art, including, e.g., with carboxylic acid, aldehyde, alcohol or halide. In certain embodiments, the capping moiety is a $C_1$-$C_{10}$ alkyl, alkenyl or alkynyl, which may be optionally substituted or is an acyl group. For example, the capping group may be methyl or acetyl. In some embodiments, the capping moiety may take the place of the N-terminal amino group; in these embodiments, the capping moiety may be H, hydroxy or an alkyl ester (including $C_1$-$C_{10}$ alkyl, alkenyl or alkynyl). In other embodiments, the capping moiety contains a sequence of amino acids, such as exopeptidase resistant sequence (e.g., $Gly_{1-5}$) (SEQ ID NO: 12). In one exemplary embodiment, the N-terminal end portion of one or both of Chains A and B comprise Ac-Y-L-, wherein Ac is acyl.

C-Terminal End Portion

The C-terminal end portion is an optional component of Chain A and/or Chain B; in some embodiments, it is the C-terminal of a mid portion or of the linker. The C-terminal end portion is a sequence of, preferably, one to five amino acids or mimetics thereof, even more preferably one, two or three amino acids or mimetics thereof. In some embodiments, the C-terminal end portion is a sequence of amino acid residues or mimetics thereof or may comprise a functional group such as a basic function group (e.g., an amine) or a hydrogen atom. The C-terminal end portion may also be a, or may include, a C-terminal capping moiety ("Z" in FIG. 2). The C-terminal end portion may be present on none, one or both of Chains A and B. In some embodiments, the C-terminal end portion comprises a moiety selected from the group consisting of a basic amino acid residue (e.g., R) and mimetics thereof, a hydrogen atom, and a basic functional group (e.g., an amine) and optionally a C-terminal capping moiety. In other embodiments, the C-terminal end portion can be a hydrogen or a polyethylene glycol ("PEG") moiety or a moiety derived from an amine, from a carboxylic acid, from an organic halide, from an alcohol or from an aldehyde. One preferred sequence is R or βA-R, optionally with a C-terminal capping moiety such as an amide.

Tail

The tail can extend the in vivo lifetime/half-life and thus the therapeutic effectiveness of the EPO mimetic. The tail is preferably attached to only the linker (which connects Chain A to Chain B), however, it is also envisioned that the tail can be attached to Chain A or Chain B. In lesser preferred embodiments, two tails are present and attached to either Chain A and Chain B, or Chain A and the linker or Chain B and the linker. In another lesser preferred embodiment, three tails are present and attached to each of Chain A, Chain B and the linker. The tail may be any useful chemical group and can easily be selected by one of skill in the art. Examples of preferred tails include polyethylene glycol ("PEG"), polypropylene glycol, polyalkylene oxide, peptide, peptide mimetic, a fatty acid moiety, transporter moiety, a hydrogen, or moieties derived from amine, from carboxylic acid, from organic halide, from alcohol and from aldehyde. The tail can be modified by functional groups, for example, PEG can be modified as shown in Harris et al., "Pegylation, A Novel Process for Modifying Pharmacokinetics", Clin. Pharmacokinet., 2001, Vol. 40(7): 539-551, which is incorporated by reference herein. If two or three tails are present, they can be the same as each other or different from each other.

Polyethylene glycol, as discussed above, is a polyalkylene glycol compound or a derivative thereof, with or without coupling agents or derivatization with coupling or activating moieties (e.g., with thiol, triflate, tresylate, azirdine, oxirane or preferably with a maleimide moiety). Compounds such as maleimido monomethoxy PEG are exemplary of activated PEG compounds. Other polyalkylene glycol compounds, such as polypropylene glycol, may be used in accordance with the present invention. Other appropriate polymer conjugates include, but are not limited to, non-polypeptide polymers, charged or neutral polymers of the following types: dextran, colominic acids or other carbohydrate based polymers, biotin derivatives and dendrimers, for example.

The PEG can be linked to an amino acid residue such as lysine, histidine, tryptophan, aspartic acid, glutamic acid and cysteine, for example, or other such amino acids (or mimetics thereof) known to those of skill in the art.

The PEG moiety, or moieties, attached to the molecule may range in molecular weight from about 200 to about 20,000 MW. In some embodiments, the PEG moiety will be from about 1,000 to 8,000 MW, from about 3,250 to 5,000

MW, or about 5,000 MW. In certain embodiments, the total molecular weight of the PEG moieties on the molecule may range from 10,000 to 50,000 MW, and may preferably be over about 30,000 MW. In some embodiments, the total molecular weight of the PEG moieties on the EPO mimetic of the invention is such that renal filtration of the compound is precluded, and in such embodiments renal clearance of the compound may be substantially reduced, such as by about ½ or less, by about ⅓ or less, by about ⅕ or less, or by about ⅒ or less, as compared to a corresponding unpegylated molecule.

The number of PEG molecules covalently bound per molecule of the invention may vary depending upon the desired stability (i.e., serum half-life), but in certain embodiments, is one, two or three PEG molecules.

Molecules disclosed herein can be linked to PEG molecules using techniques shown in, but not limited to, U.S. Pat. Nos. 4,179,337; 5,382,657; 5,972,885; 6,177,087; 6,165,509; 5,766,897; and 6,217,869, each of which are incorporated herein by reference.

In other embodiments, other moieties may be attached to EPO mimetics of the invention to extend serum half-life of the mimetics. For instance, human serum albumin, transferrin, Ig segments or other serum proteins may be attached, linked or conjugated to EPO mimetics of the invention. Such molecules and methods of attachment are known in the art and are described, e.g., in U.S. Pat. Nos. 7,238,667; 7,176,278; and 5,766,883, each of which is incorporated herein by reference.

Other moieties that may be used to extend the half-life of the EPO mimetics of the present invention can be found on pages 42-43 of U.S. Provisional Application Ser. No. 61/487,760, filed May 19, 2011, which is incorporated herein by reference and to which the present application claims priority.

The compounds of the present invention may employ various natural or non-natural amino acids, i.e., amino acids other than the standard, genetically-encoded amino acids, and/or may employ amino acid mimetics, such as substitute replacements of moieties in the peptide backbone, all of which are more fully described on pages 47-51 of U.S. Provisional Application Ser. No. 61/487,760, filed May 19, 2011, which is incorporated herein by reference and to which the present application claims priority.

In a preferred embodiment, the N-terminal end portion is Ac-N-Y-L, the loop is R-M-P-X-V (SEQ ID NO: 11) and the C-terminal end portion is X-P-R where X is homo-arginine; the tail is preferably PEG, a fatty acid or hSA binding peptide. This preferred embodiment may be about 10× more active than prior art rhEPO or EPO with an in vitro affinity of <1 nM (600 pM) as determined by radiolabeled competition assay.

Pharmaceutical Compositions

The EPO mimetics of the invention are useful for the preparation of pharmaceutical compositions for stimulating erythropoiesis in a patient. Thus, the EPO mimetics of the present invention are useful for treating and/or preventing various conditions associated with decreased red-blood cell count. For example, the EPO mimetics of the invention are useful for treating renal insufficiency and/or end-stage renal failure; anemia, including anemia associated with cancer chemotherapy, AIDS treatment (e.g., treatment with AZT or other reverse transcriptase inhibitors), chronic inflammatory disease, or an autoimmune disease; and for boosting the red blood count of a patient prior to surgery. The EPO mimetic compounds of the invention may also be useful in diagnostic applications and/or in other applications, including for research uses.

Pharmaceutical compositions according to the present invention may be formulated for administration by inhalation (via mouth or nose), oral, parenteral, transdermal or transmucosal means; parenteral modes of administration are preferred. In general, pharmaceutical compositions according to the present invention may comprise effective amounts of an EPO mimetic according to the present invention (or derivative products thereof) together with pharmaceutically acceptable excipients, diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 20, Tween 80, Polysorbate 80), anti-oxidants (e.g., ascorbic acid, sodium metabisulfite), preservatives (e.g., thimersol, benzyl alcohol) and bulking substances (e.g., lactose, mannitol). Such compositions may influence the physical state, stability, rate of in vivo release and rate of in vivo clearance of the EPO mimetics. The pharmaceutical composition according to the present invention may be prepared in liquid form or may be in dried powder (e.g., lyophilized) form.

Preferred methods of administration of EPO mimetics of the present invention may be parenteral (intramuscular, intraperitoneal, intravenous or subcutaneous injection). Preparations according to this invention for parenteral administration include sterile aqueous or non-aqueous solutions, suspensions or emulsions. Examples of non-aqueous solvents or vehicles are propylene glycol, polyethylene glycol, vegetable oils such as olive oil and corn oil, gelatin and injectable organic esters such as ethyl olate. Such dosage forms may also contains adjuvants such as preserving, wetting, emulsifying and dispersing agents. They may be sterilized by, e.g., filtration through a bacteria retaining filter, by incorporating sterilizing agents into the compositions, by irradiating the compositions, or by heating the compositions. They can also be manufactured using sterile water, or some other sterile injectable medium, immediately before use.

An especially preferred method of administration is through the use of a micro needle with a pen-style dosing cartridge as is currently used for BYETTA® (exenatide). Such a delivery would allow a patient to self-treat. A therapeutically effective dose could be contained within about 20 μl of fluid. It is envisioned that such a delivery device could be coupled with a monitoring device to allow the patient to monitor the patient's hematocrit changes; such a monitoring device could be a readily-available, non-invasive finger cuff for hemoglobin levels (surrogate for hematocrit).

One of skill in the art on considering the therapeutic context, age and general health of the recipient, will be able to ascertain proper dosing; the selected dosage depends upon the desired therapeutic effect, on the route of administration and on the duration of the treatment desired. Generally, dosage levels of 0.001 to 10 mg/kg of body weight daily are administered to mammals; dosage may be lower for intravenous injection or infusion. The dosing schedule may vary depending on the circulation half-life and the formulation used.

The EPO mimetics of the present invention may be administered in conjunction with one or more additional active ingredients or pharmaceutical compositions.

Methods of Treatment

The present invention also relates to methods of treatment using the EPO mimetics of the present invention.

More particularly, the EPO mimetics of the present invention may be administered to warm blooded animals, preferably mammals, more preferably humans, to simulate the binding of EPO to the EPOR in vivo. Thus, the present invention provides methods for therapeutic treatment of disorders associated with a deficiency of EPO, which methods comprise administering a EPO mimetic of the invention in amounts sufficient to stimulate the EPOR and thus alleviate the symptoms associated with a deficiency of EPO in vivo. For example, the EPO mimetics of this invention will find use in the treatment of renal insufficiency and/or end-stage renal failure/dialysis; anemia associated with AIDS; anemia associated with chemotherapy for cancer; anemia associated with chronic inflammatory disease (e.g., rheumatoid arthritis and chronic bowel inflammation); anemia associated with autoimmune disease; and for boosting the red blood count of a patient prior to surgery. Other disease states, disorders and states of hematologic irregularity that may be treated by administration of the EPO mimetics of this invention include: beta-thalassemia; cystic fibrosis; pregnancy and menstrual disorders; early anemia of prematurity; spinal cord injury; space flight; acute blood loss; aging; stroke and/or ischemia (both CNS and cardiac); and various neoplastic disease states accompanied by abnormal erythropoiesis.

In other embodiments, the EPO mimetics of the present invention may be used for the treatment of disorders which are not characterized by low or deficient red blood cells, e.g., as a pretreatment prior to transfusions. In addition, administration of the EPO mimetics of the present invention can result in a decrease in bleeding time and will thus find a use in the administration to patients prior to surgery or for indications wherein bleeding is expected to occur. In addition, the EPO mimetics of the present invention will find use in the activation of megakaryocytes.

Since EPO has been shown to have a mitogenic and chemotactic effect on vascular endothelial cells as well as an effect on central cholinergic neurons (see, e.g., Amagnostou et al., Proc. Natl. Acad. Sci. USA, 1990, Vol. 87, pp. 5978-5982; Konishi et al., Brain Res., 1993, Vol. 609, pp. 29-35), the EPO mimetics of this invention will also find use in the treatment of a variety of vascular disorders, such as: promoting wound healing; promoting growth of collateral coronary blood vessels (such as those that may occur after myocardial infarction); trauma treatment; and post-vascular graft treatment. The EPO mimetics of the present invention will also find use for the treatment of a variety of neurological disorders, generally characterized by low absolute levels of acetyl choline or low relative levels of acetyl choline as compared to other neuroactive substances, e.g., neurotransmitters.

Methods of Synthesis

The present invention also provides a method for preparing compounds having the general structure depicted in FIG. 1. Compounds of the invention can be prepared by convergent three-fragment assembly strategy. Two of the fragments can each include a turn defined by a loop and an intrachain bridge covalently linked across the loops, for example between $L_1$ and $L_2$ components in Chain A and/or Chain B. A third fragment can incorporate a linker component and two functional groups for coupling to the two fragments comprising Chain A and Chain B, respectively. Chain A and Chain B can be similar or identical and coupled simultaneously (e.g., in a single, concurrent reaction) to the linker.

Alternatively, Chain A and Chain B can be different (e.g., in terms of sequence) and coupled sequentially (e.g., in separate reactions) to the linker by use of orthogonal protecting groups or other suitable chemistries known to those skilled in the art.

Figure 3:
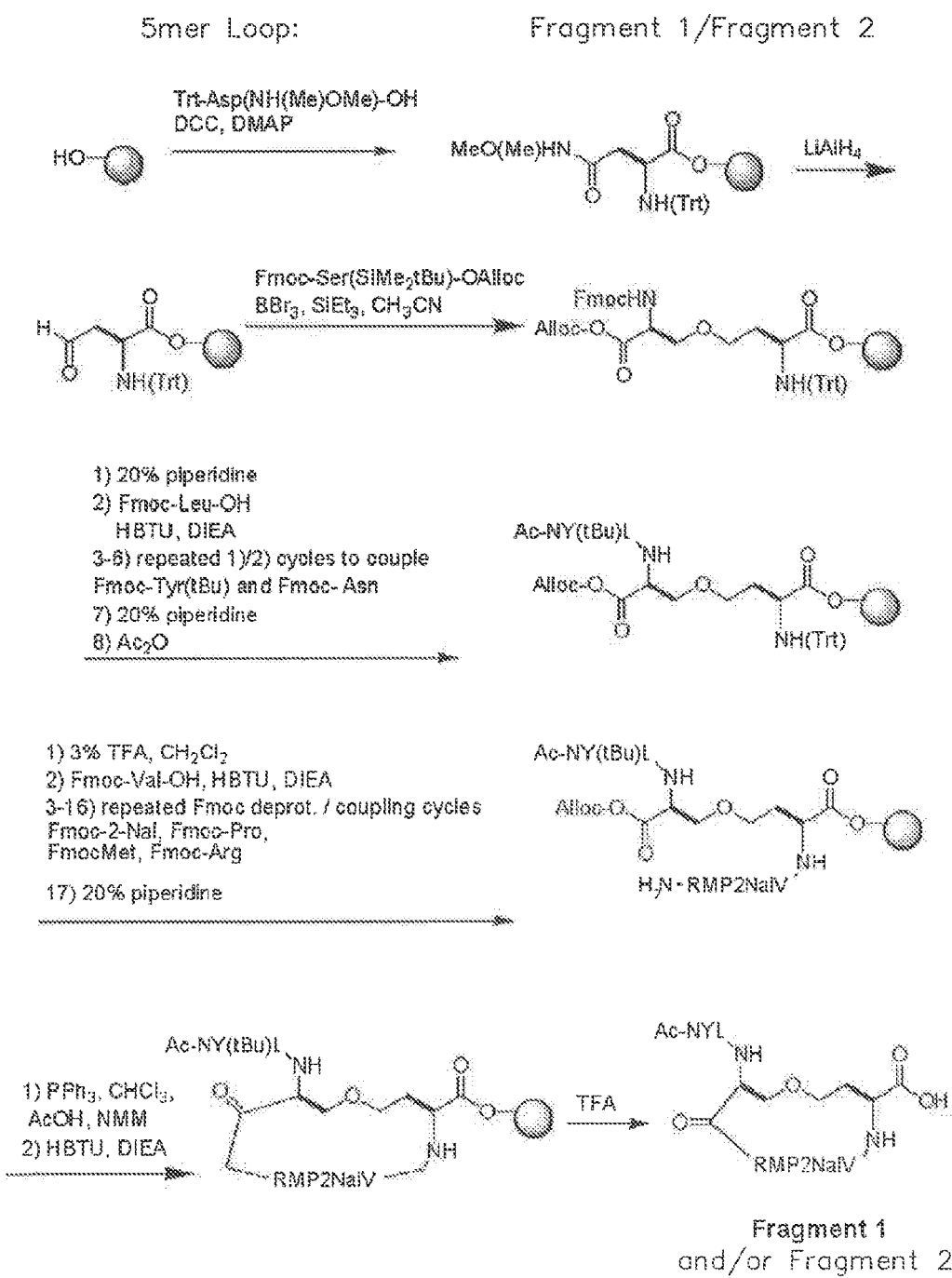
FIGS. 3-5 illustrate an exemplary strategy for preparing EPO mimetic compounds of the present invention by a stepwise solid-phase coupling approach (C→N direction)

An exemplary method of preparation is depicted in the preparation of fragment 1 or fragment 2 (as fragments of Chain A or Chain B, respectively) in FIG. 3. Briefly, (i) a bridge structure (such as an ether-containing bridge structure) can be formed using solid-phase synthesis on a solid support; (ii) an N-terminal end portion can be covalently coupled to or stepwise synthesized by sequential addition to the bridge structure; (iii) a loop sequence can be covalently coupled to or stepwise synthesized by sequential addition to the bridge structure (e.g., at a first end thereof); and (iv) the loop sequence can be cyclized to the bridge structure (e.g., at a second end thereof).

Hence, more specifically, e.g., a protected monomer, such as trityl-Asp(NH(Me)OMe)-OH can be coupled to a resin via its C-terminal acid. The activated sidechain amide can be reduced to an aldehyde with a reducing agent such as lithium aluminum hydride. An ether bridge precursor component can then be formed by reaction of the aldehyde with the silyl ether (e.g., Fmoc-Ser(SiMe$_2$tBu)-(OAlloc) in the presence of a suitable catalyst system (e.g., BiBr$_3$ and triethylsilane, or alternatively Et$_3$SiBr) in a suitable solvent (e.g., acetonitrile or dichloromethane) by reductive etherification methods.

Following Fmoc deprotection, additional monomers of the N-terminal end component can be coupled sequentially by standard solid phase peptide synthesis methodologies. In an exemplary method, the end component can be coupled to the resin as one fragment, previously synthesized on a suitable resin and purified by HPLC.

The N-terminal amine can be capped by acetylation with acetic anhydride. At this point, the N-trityl protected amine can be orthogonally deprotected with 3% TFA/CH$_2$Cl$_2$ and a sequence of monomers corresponding to the loop component are coupled sequentially by standard solid phase peptide synthesis methodologies.

In an exemplary method, the loop component can be coupled to the resin as one fragment, previously synthesized on a suitable resin and purified by HPLC.

Following N-Fmoc and C-Alloc ester deprotections, cyclization of the loop component to the $L_2$ component can be achieved by activating the carboxylic acid group with a coupling reagent such as HBTU, washing away excess reagents, and allowing a reaction with the free amine at room temperature overnight.

In an exemplary method, the cyclization can be performed at approximately 4° C. to 80° C. for between about 30 minutes to about 36 hours. In an exemplary method, the cyclization can be carried out under microwave irradiation.

In an exemplary method, fragment 1 or fragment 2 (Chain A or Chain B) can be cleaved from the resin by TFA giving a fully sidechain-deprotected fragment 1 or fragment 2 (Chain A or Chain B) suitable for coupling by the disclosed convergent fragment assembly strategy. In an exemplary method, fragment 1 or fragment 2 can be cleaved from the resin with retention of acid-labile sidechain protecting groups ready for coupling by the convergent fragment assembly strategy.

It will be appreciated by those skilled in the art that the monomers for the mid component can be easily included into the fragment 1 or fragment 2 (Chain A or Chain B) synthesis by standard SPPS methodologies at an appropriate point in the sequence.

The cleaved fragment 1 or fragment 2 (Chain A or Chain B) can be purified by HPLC by standard methods well known in the art before further couplings.

Figure 4:
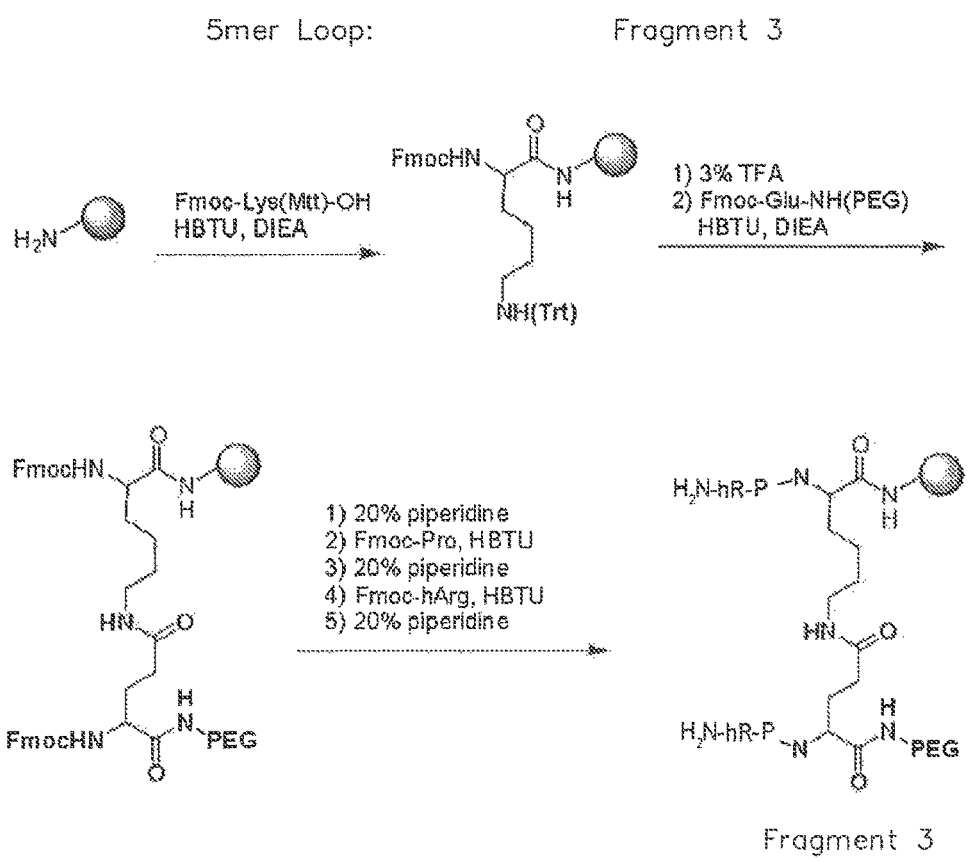

In an exemplary method, a fragment 3 comprising a linker moiety can be prepared as illustrated in FIG. 4 by coupling through α-carbon side chains of amino acids. As depicted, a fragment 3 can be prepared by coupling Fmoc-Lys(Mtt)-OH to a Rink-linker-resin. Following Mtt deprotection with 3% TFA, Fmoc-Glu-NH(PEG) can be coupled to the γ-amino group via its sidechain acid. Double Fmoc deprotection and standard Fmoc SPPS can be used to couple Fmoc-Pro and Fmoc-Lys(Boc) monomers to each amine. It will be appreciated by those skilled in the art that the monomer sequence for the mid component could be included either in fragment 1 and/or fragment 2 (Chain A and Chain B) syntheses or fragment 3 synthesis. Double Fmoc deprotection gives two functional groups (amines) for couplings to fragment 1 and fragment 2 (Chain A and Chain B). It will be appreciated by those skilled in the art that fragment 3 could also be cleaved from the resin, purified by HPLC and utilized in solution-phase fragment couplings.

Figure 5:
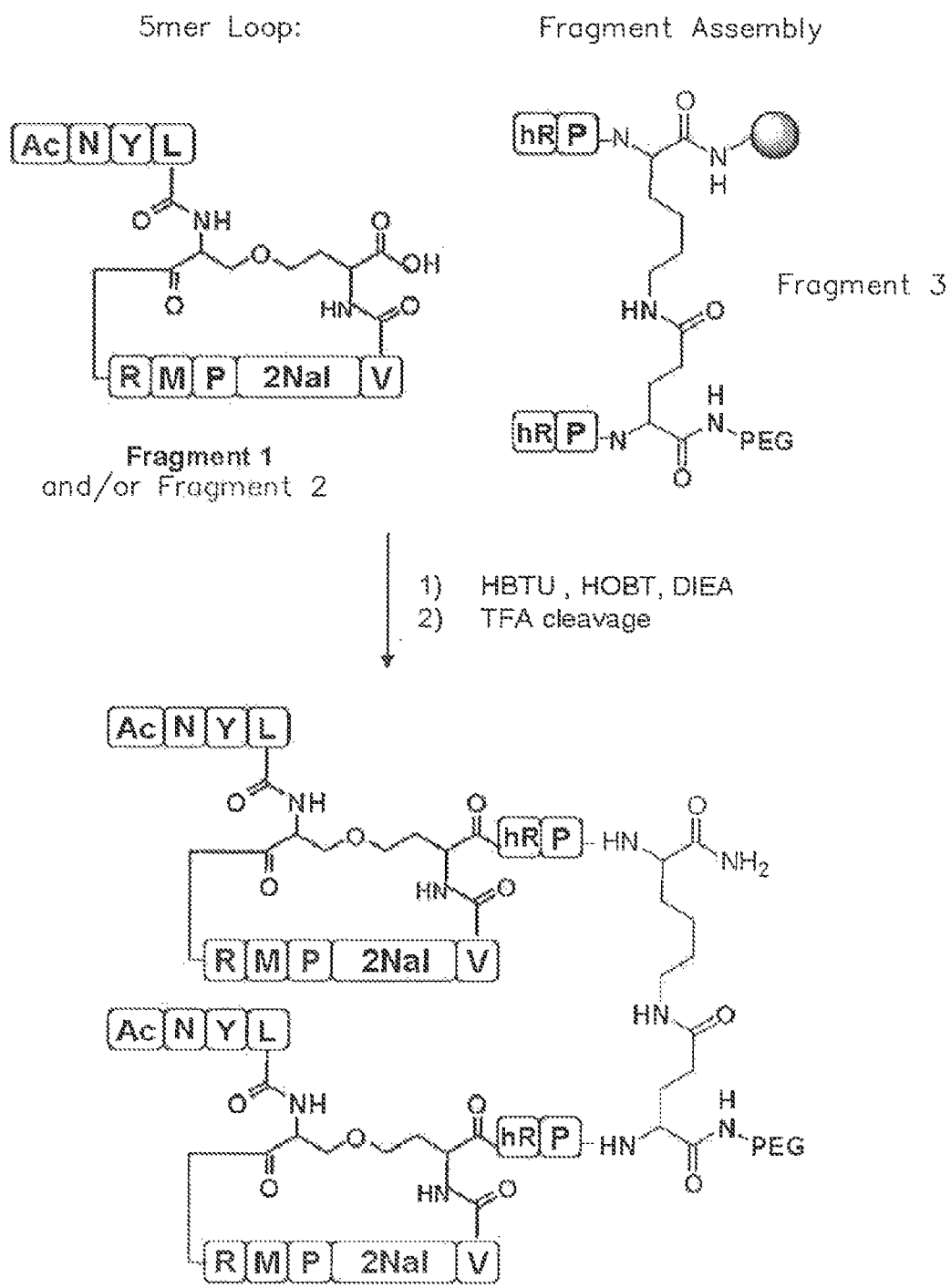
Figure 6:
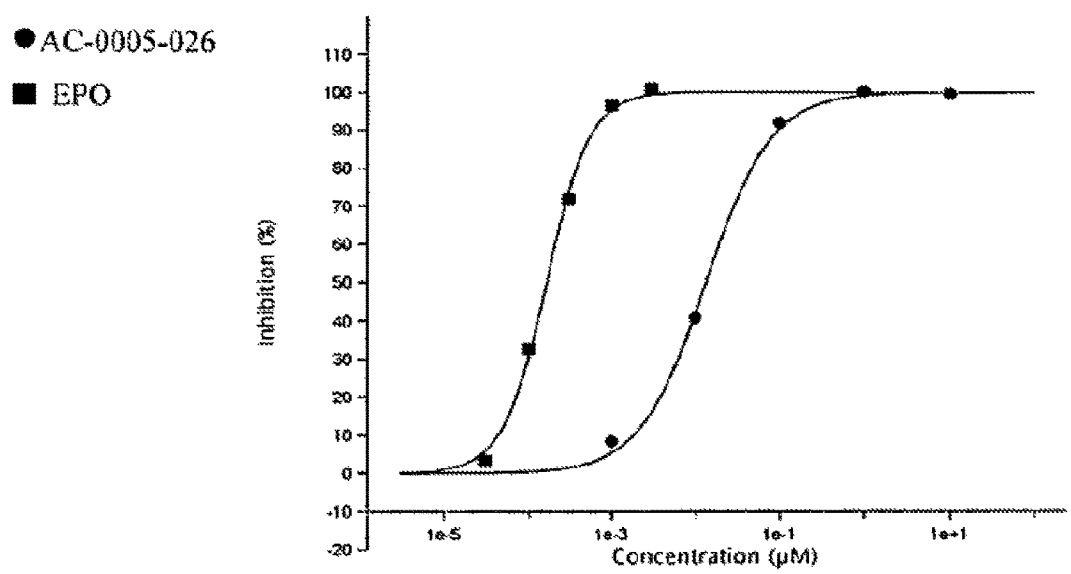
FIG. 6 illustrates the response curve of an assay carried out on EPO mimetic AC-0005-026 (SEQ ID NO 7).
Figure 7:
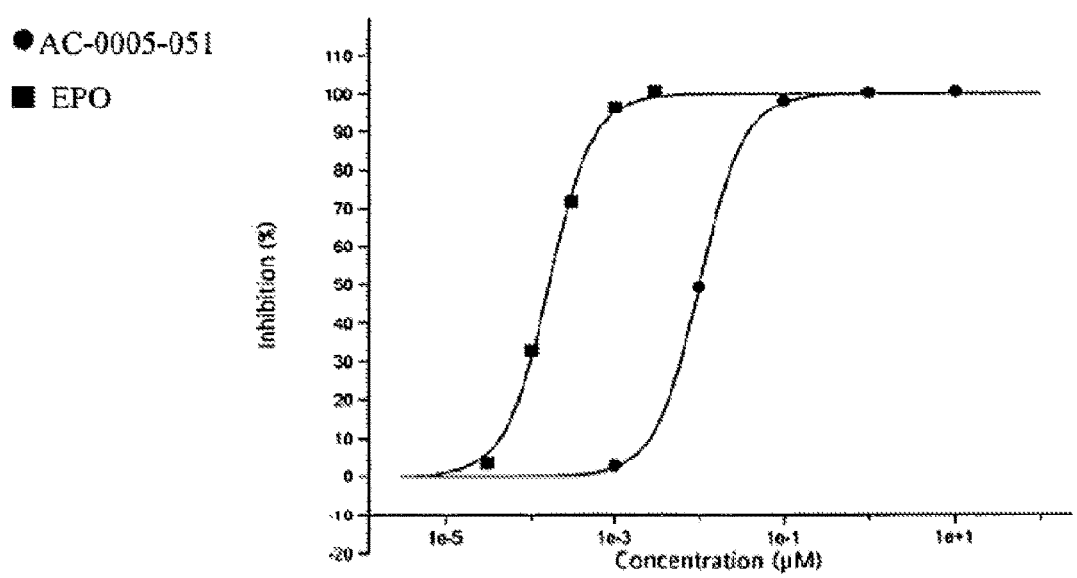
FIG. 7 illustrates the response curve of an assay carried out on EPO mimetic AC-0005-051 (SEQ ID NO 7).
Figure 8:
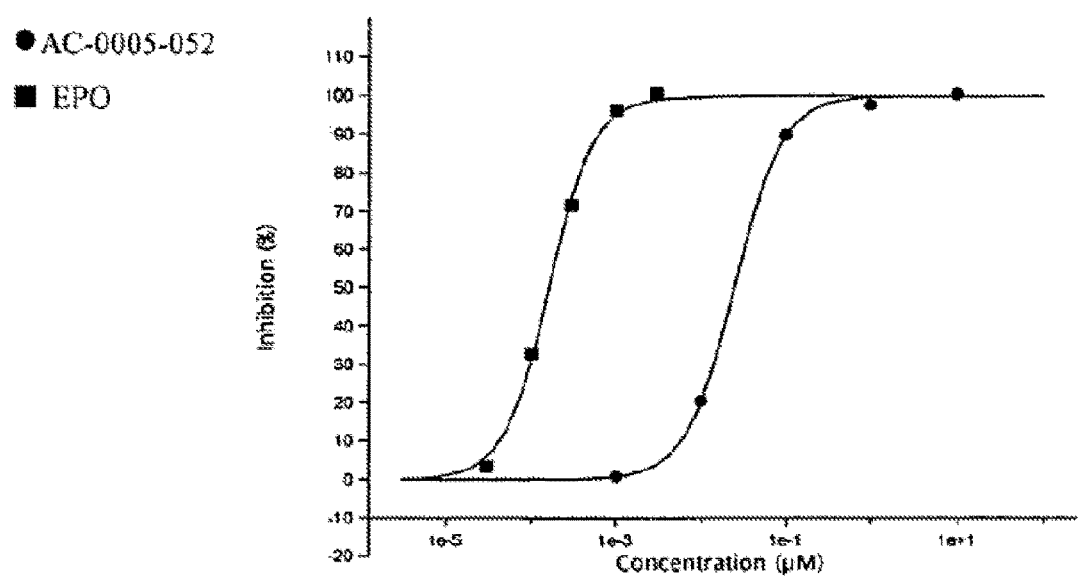
FIG. 8 illustrates the response curve of an assay carried out on EPO mimetic AC-0005-052 (SEQ ID NO 7).
Figure 9:
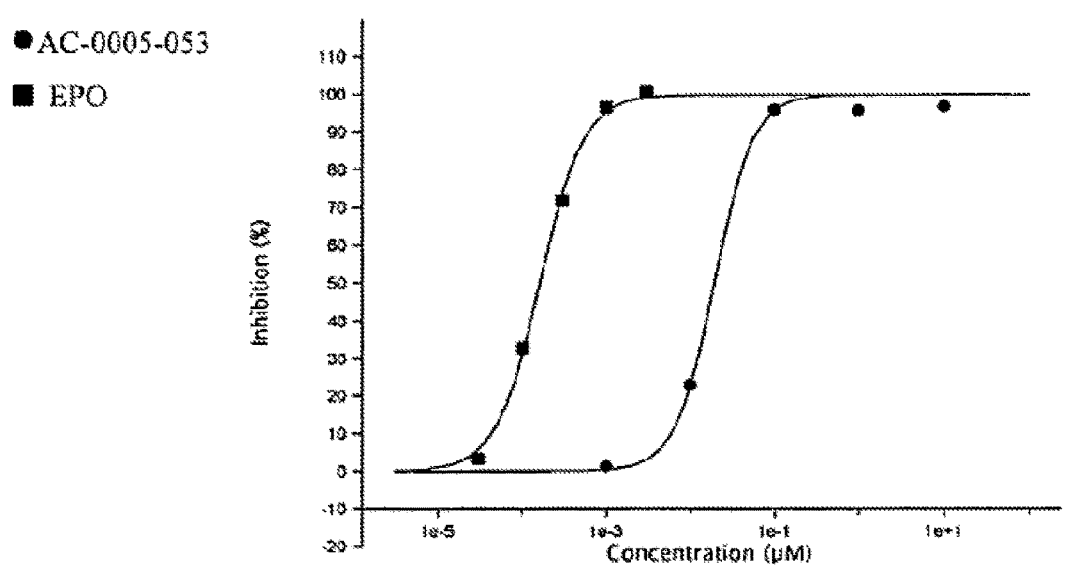
FIG. 9 illustrates the response curve of an assay carried out on EPO mimetic AC-0005-053 (SEQ ID NO 7).
Figure 10:
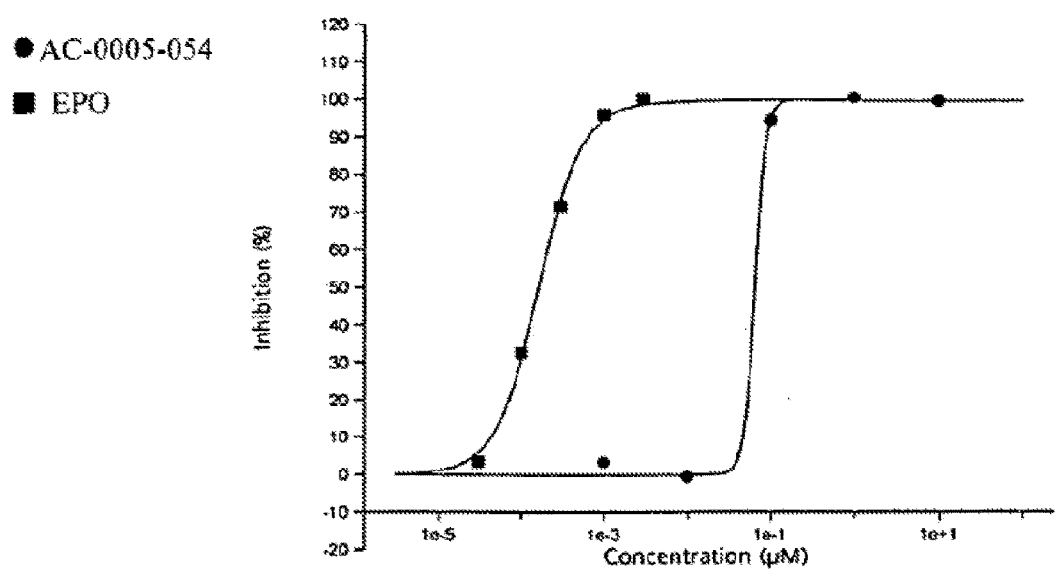
FIG. 10 illustrates the response curve of an assay carried out on EPO mimetic AC-0005-054 (SEQ ID NO 8).
Figure 11:
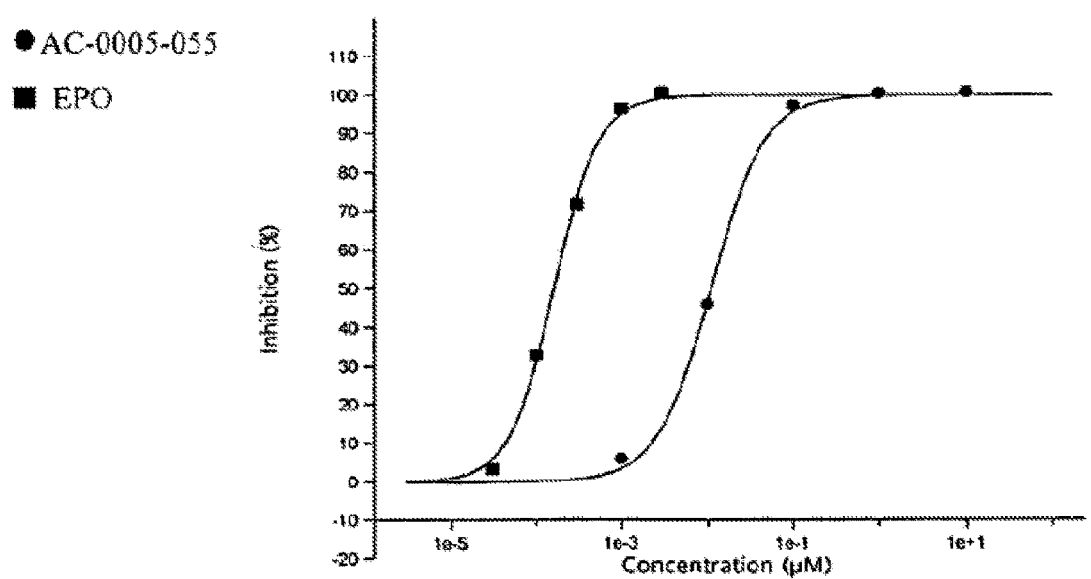
FIG. 11 illustrates the response curve of an assay carried out on EPO mimetic AC-0005-055 (SEQ ID NO 24).
Figure 12:
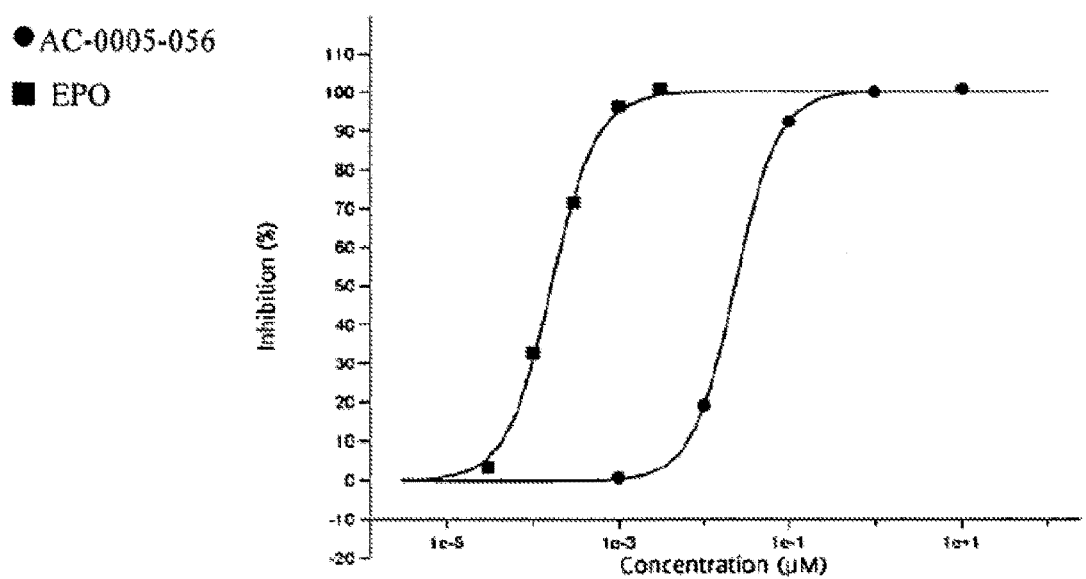
FIG. 12 illustrates the response curve of an assay carried out on EPO mimetic AC-0005-056 (SEQ ID NO 25).
Figure 13:
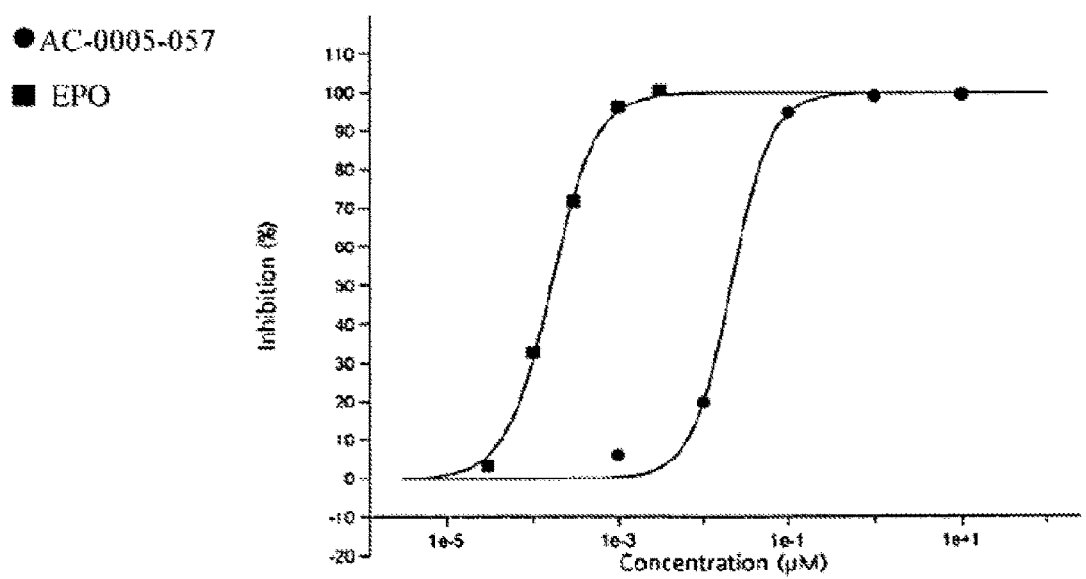
FIG. 13 illustrates the response curve of an assay carried out on EPO mimetic AC-0005-057.

Ideally, when fragment 1 and fragment 2 are structurally the same (or substantially the same), then two equivalents of fragment 1/2 (Chain A=Chain B) are activated by reagents such as HBTU/HOBT/DIEA and coupled to immobilized fragment 3, as depicted in FIG. 5. The novel compound can be cleaved from the resin and fully deprotected. It will be appreciated by those skilled in the art that these fragment couplings could be performed in solution-phase. It will be further appreciated by those skilled in the art that, when fragment 1 and fragment 2 (comprising Chain A and Chain B, respectively) are structurally different they can be coupled sequentially (e.g., in separate reactions) to fragment 3 (the linker-containing fragment), for example by use of orthogonal protecting groups or chemistries.

EXAMPLES

Several series of assays were carried out on various EPO mimetics. For the assays in Examples 1-4, the EPOR used was obtained as follows:

| | |
|---|---|
| Source: Human recombinant NSO cells | Ligand: 0.04 nM [$^{125}$I] Erythropoietin |
| Vehicle: 1% DMSO | Incubation Time/Temp: 2 hours @25° C. |
| Incubation Buffer: 1.5 mM KH$_2$PO$_4$, 8 mM Na$_2$HPO$_4$•H$_2$O, pH 7.4, 137 mM NaCl, 2.7 mM KCl, 0.2% BSA | Non-Specific Ligand: 3 nM Erythropoietin |
| | $K_f$: 0.036 nM |
| | $B_{MAX}$: 3000 pmole/mg Protein |
| Specific Binding: 89% | Quantitation Method: Radioligand Binding |
| Significance Criteria: ≥50% of max stimulation or inhibition | |

Example 1

A series of assays was carried out on several EPO mimetics that varied in their N-terminal end portion, loop and C-terminal end portion sequences ("Loop" sequences disclosed as SEQ ID NOS 13, 1-2, 1, 1, 3-5, 14, 7, 7, 7, 7, 7, 8, 11, and 15, respectively, in order of appearance). The results are as follows:

| | N-End | Loop | Mid | Ki nM |
|---|---|---|---|---|
| 1. | AcNYL | RMGPITWV | KP | 48 (control) |
| 2. | AcNYL | RMGWV | KP | 22 |
| 3. | AcNYL | RMβAWV | KP | 27 |
| 4. | AcNYL | RMGWV | RP | 44 |

-continued

| | N-End | Loop | Mid | Ki nM |
|---|---|---|---|---|
| 5. | AcNYL | RMGWV | homoRP | 12 |
| 6. | AcNYL | RMFWV | RP | 17 |
| 7. | AcNYL | RMhomoFWV | RP | 17 |
| 8. | AcNYL | RMLWV | RP | 34 |
| 9. | AcNYL | RMhomoLWV | RP | 23 |
| 10. | AcNYL | RMPWV | RP | 9 |
| 11. | EPO | | | 0.08 (control) |
| 12. | AcNYL | RMPWV | KP | 5.9 |
| 13. | AcNYL | RMPWV | homoRP | 4.6 |
| 14. | AcYL | RMPWV | KP | 11.4 |
| 15. | Desamino YL | RMPWV | KP | 9.6 |
| 16. | AcNYL | HMPWV | KP | 15.5 |
| 17. | AcNYL | RMPXV | KP | 4.8 |
| 18. | AcNYL | HMPZV | KP | 11.2 |

Example 2

A series of assays was carried out on several EPO mimetics that varied in their loop, C-terminal end portion and tail sequences, and the results are as follows ("Loop" sequences disclosed as SEQ ID NOS 7, 11, 11, 11, 11, 11, and 11, respectively, in order of appearance):

| | N-End | Loop | Mid | C-end | Ki nM |
|---|---|---|---|---|---|
| 19. | EPO | | | | 0.06 |
| 20. | AcNYL | RMPWV | KP | | 4.3 (control) |
| 21. | AcNYL | RMPXV | KP | | 6 (control) |
| 22. | AcNYL | RMPXV | homoRP | R | 19.8 |
| 23. | AcNYL | RMPXV | KP | R | 27.7 |
| 24. | AcNYL | RMPXV | KP | βAR | 1.2 |
| 25. | AcNYL | RMPXV | homoRP | βAR | 1 |
| 26. | AcNYL | RMPXV | homoRP | | 0.6 |

Results show that a close to optimal EPO mimetic has a $K_i \approx 600$ pMolar.

Various EPO mimetics were evaluated in Radioligand Binding assays, using methods adapted from the scientific literature [Broudy et al., *Erythropoietin receptor characteristics on primary human erythroid cells*, Blood, 1991, Vol. 77(12):2583-2590; Harris et al., *Ligand binding properties of human erythropoietin receptor extracellular domain expressed in Escherichia coli*, J. Biol. Chem., 1992, Vol. 267(21):15205-15209, both of which are incorporated by reference].

IC$_{50}$ values were determined by a non-linear, least squares regression analysis using MATHIQ™ (computer software for integrating mathematical functions into new or existing software). K$_I$ values were calculated using the equation of Cheng and Prusoff (Biochem. Pharmacol., 1973, Vol. 22, pp. 3099-3108), using the observed IC$_{50}$ of the tested compound, the concentration of the radioligand employed in the assay, and the historical values for the K$_i$ of the ligand. Where presented, the Hill coefficient (n$_H$), defining the slope of the competitive binding curve, was calculated using MATHIQ™. Hill coefficients significantly different than 1.0 may suggest that the binding displacement does not follow the laws of mass action with a single binding site. Where IC$_{50}$, K$_I$ and/or n$_H$ data was presented without Standard Error of the Mean (SEM), data are insufficient to be quantitative, and the values presented (K$_I$, IC$_{50}$ and n$_H$) should be interpreted with caution.

For the assays in Examples 3 and 4, the identifiers correspond to EPO mimetic structures as follows (circles such as "○" between amino residues or mimetics thereof represent bonds):

| Identifier
EPO | Structure
(standard) |
|---|---|
| AC-0005-001
(SEQ ID NOS 16 and 16) | Ac-NH-GGNYLCRMGPITWVCKPQGG-C(=O)-NH-CH(C(=O)NH₂)-(CH₂)₄-NH-C(=O)-(CH₂)₄-NH-C(=O)-GGNYLCRMGPITWVCKPQGG-NH-Ac (two chains linked via lysine side chain; each chain contains an intramolecular S–S disulfide between the two Cys residues) |
| AC-0005-002
(SEQ ID NOS 17 and 17) | Ac-NH-GGLYACHMGPITT(1Nal)VCQPQGG-C(=O)-NH-CH(C(=O)NH₂)-(CH₂)₄-NH-C(=O)-(CH₂)₄-NH-C(=O)-GGNYLCHMGPITT(1Nal)VCQPQGG-NH-Ac (two chains linked via lysine side chain; each chain contains an intramolecular S–S disulfide) |
| AC-0005-003
(SEQ ID NOS 18 and 18) | Ac-NH-NYLCRMGPITWVCKP-C(=O)-NH-CH(C(=O)NH₂)-(CH₂)₄-NH-C(=O)-(CH₂)₄-NH-C(=O)-NYLCRMGPITWVCKP-NH-Ac (two chains linked via lysine side chain; each chain contains an intramolecular S–S disulfide between the two Cys residues) |

| Identifier EPO | Structure (standard) |
|---|---|
| AC-0005-004 (SEQ ID NOS 19 and 19) | 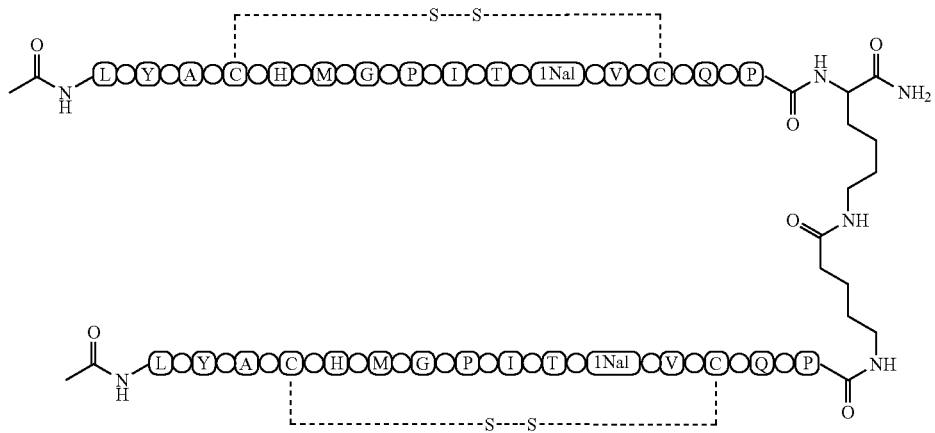 |
| AC-0005-005 (SEQ ID NOS 20 and 20) | 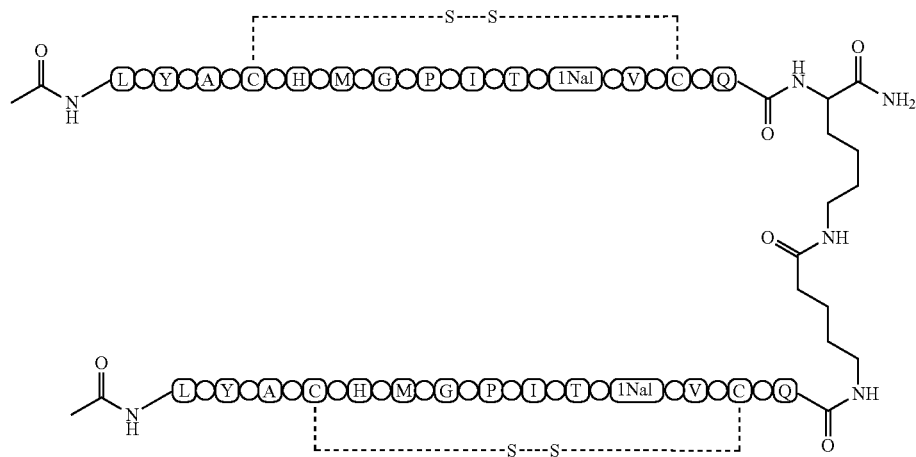 |
| AC-0005-006 (SEQ ID NOS 21 and 21) | 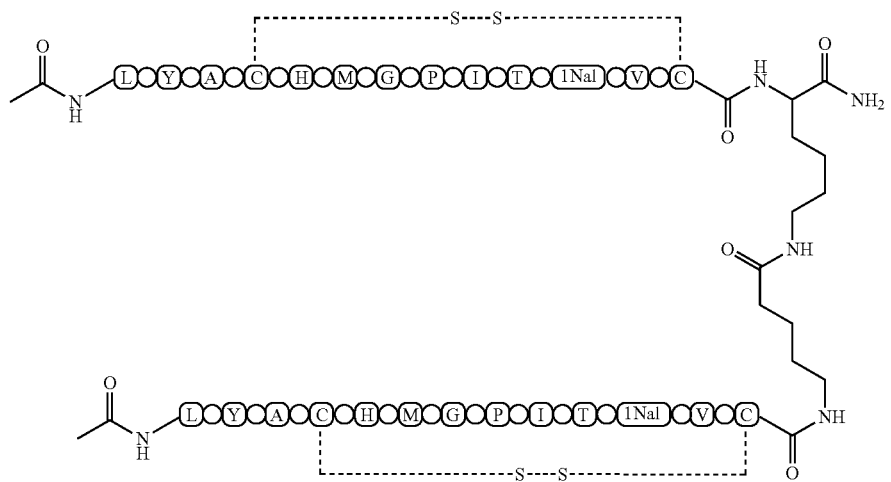 |

-continued
| Identifier EPO | Structure (standard) |
|---|---|
| AC-0005-007 (SEQ ID NOS 22 and 22) | 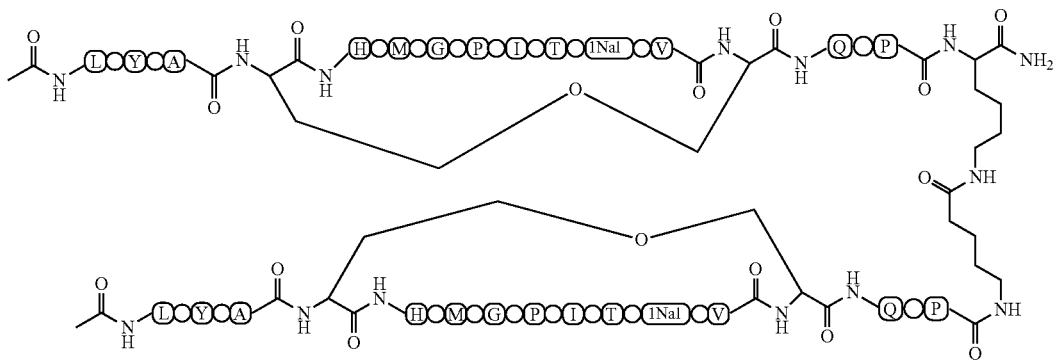 |
| AC-0005-008 (SEQ ID NOS 23 and 23) | 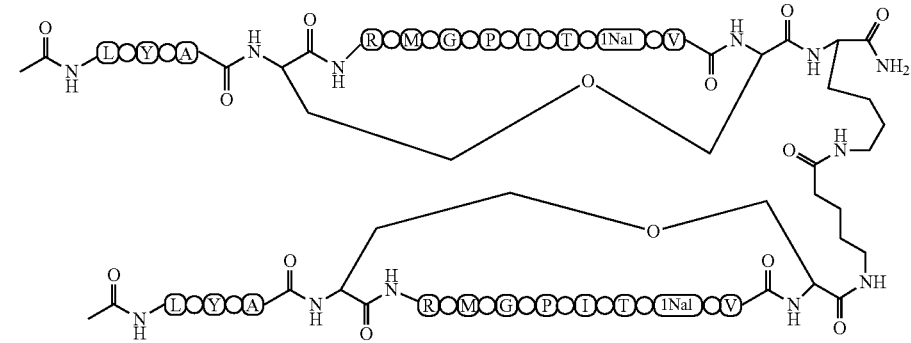 |
| AC-0005-018 (SEQ ID NOS 1 and 1) | 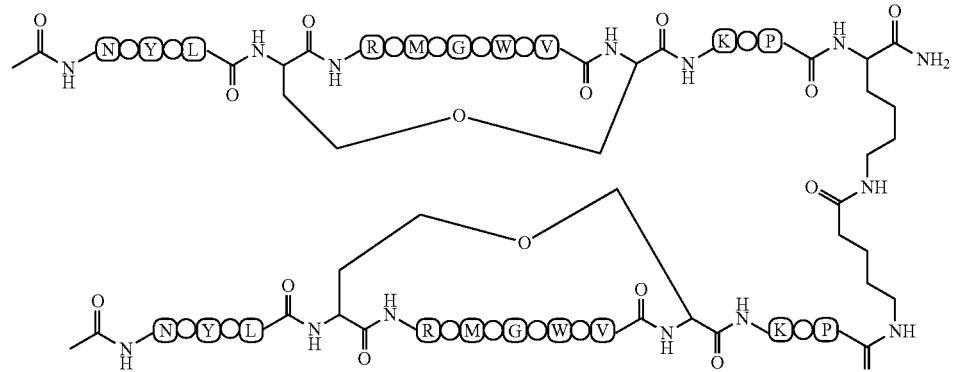 |
| AC-0005-019 (SEQ ID NOS 2 and 2) | 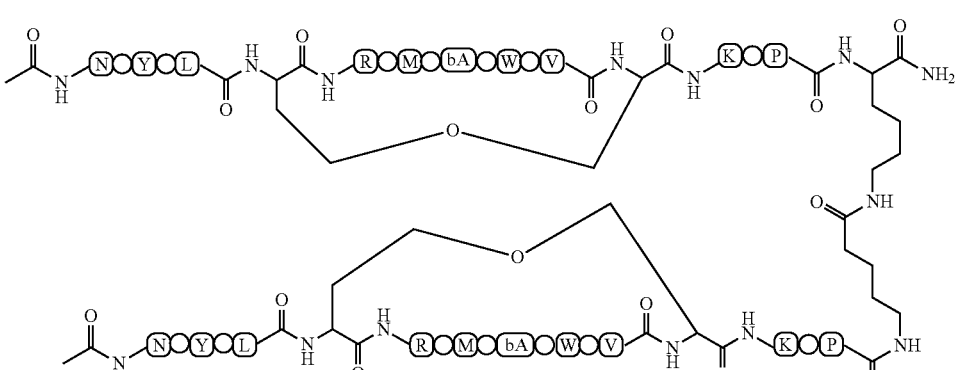 |

| Identifier EPO | Structure (standard) |
|---|---|
| AC-0005-020 (SEQ ID NOS 1 and 1) | |
| AC-0005-021 (SEQ ID NOS 1 and 1) | |
| AC-0005-022 (SEQ ID NOS 3 and 3) | |
| AC-0005-023 (SEQ ID NOS 4 and 4) | |

| Identifier EPO | Structure (standard) |
|---|---|
| AC-0005-024 (SEQ ID NOS 5 and 5) | 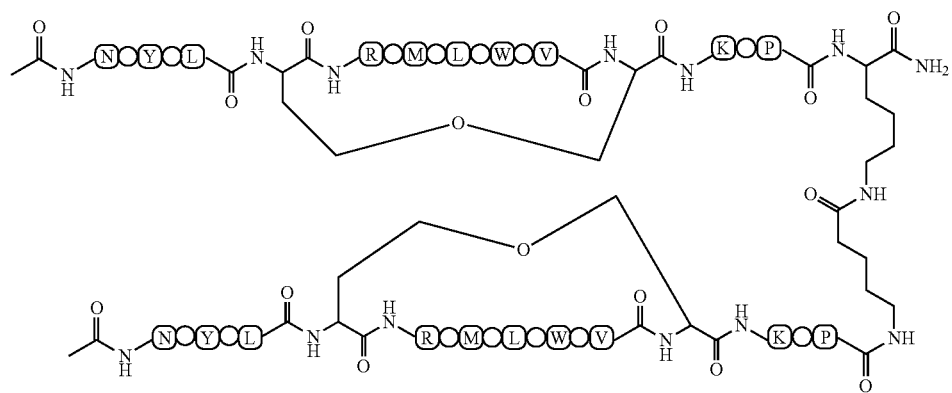 |
| AC-0005-025 (SEQ ID NOS 6 and 6) | 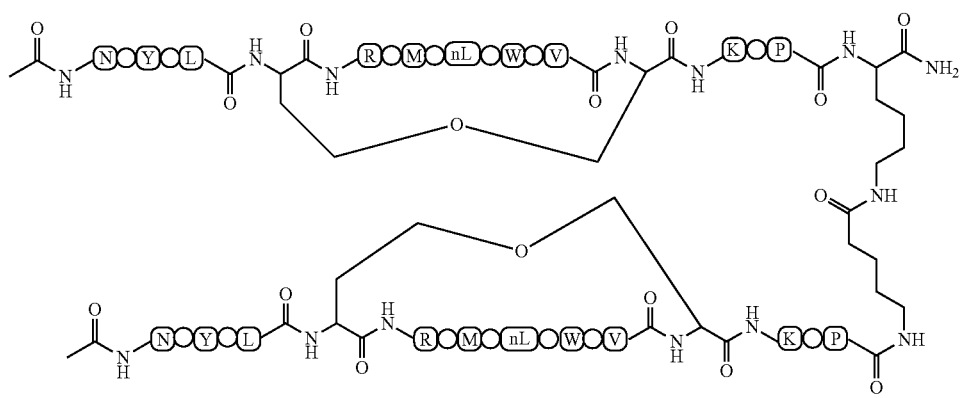 |
| AC-0005-026 (SEQ ID NOS 7 and 7) | 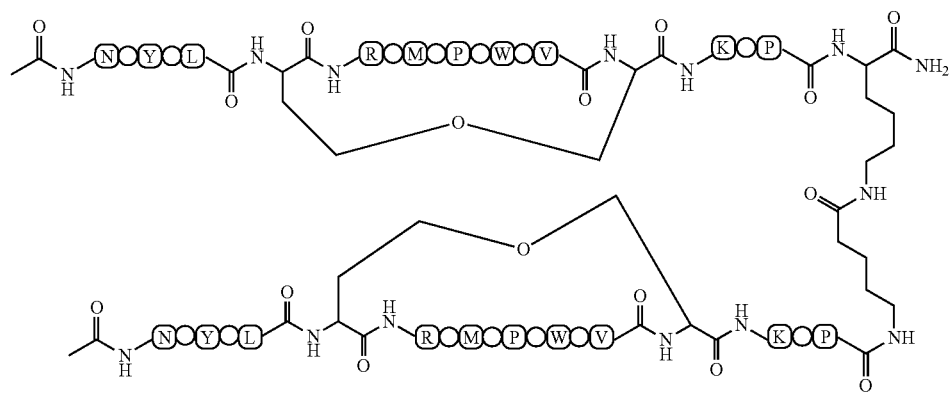 |

| Identifier<br>EPO | Structure<br>(standard) |
|---|---|
| AC-0005-051<br>(SEQ ID NOS 7 and 7) | 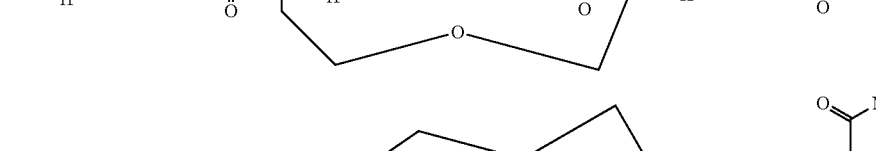 |
| AC-0005-052<br>(SEQ ID NOS 7 and 7) | 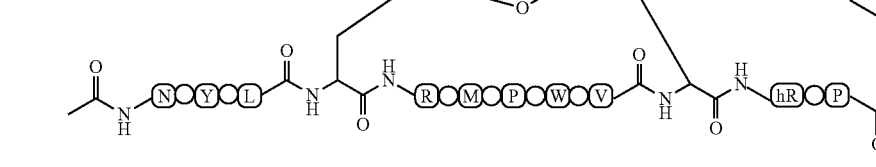 |
| AC-0005-053<br>(SEQ ID NOS 7 and 7) |  |

| Identifier
EPO | Structure
(standard) |
|---|---|
| AC-0005-054 (SEQ ID NOS 8 and 8) | |
| AC-0005-055 (SEQ ID NOS 24 and 24) | |
| AC-0005-056 (SEQ ID NOS 25 and 25) | |

| Identifier EPO | Structure (standard) |
|---|---|
| AC-0005-057 | |
| AC-0005-060 (SEQ ID NOS 24 and 24) | |
| AC-0005-061 (SEQ ID NOS 24 and 24) | |

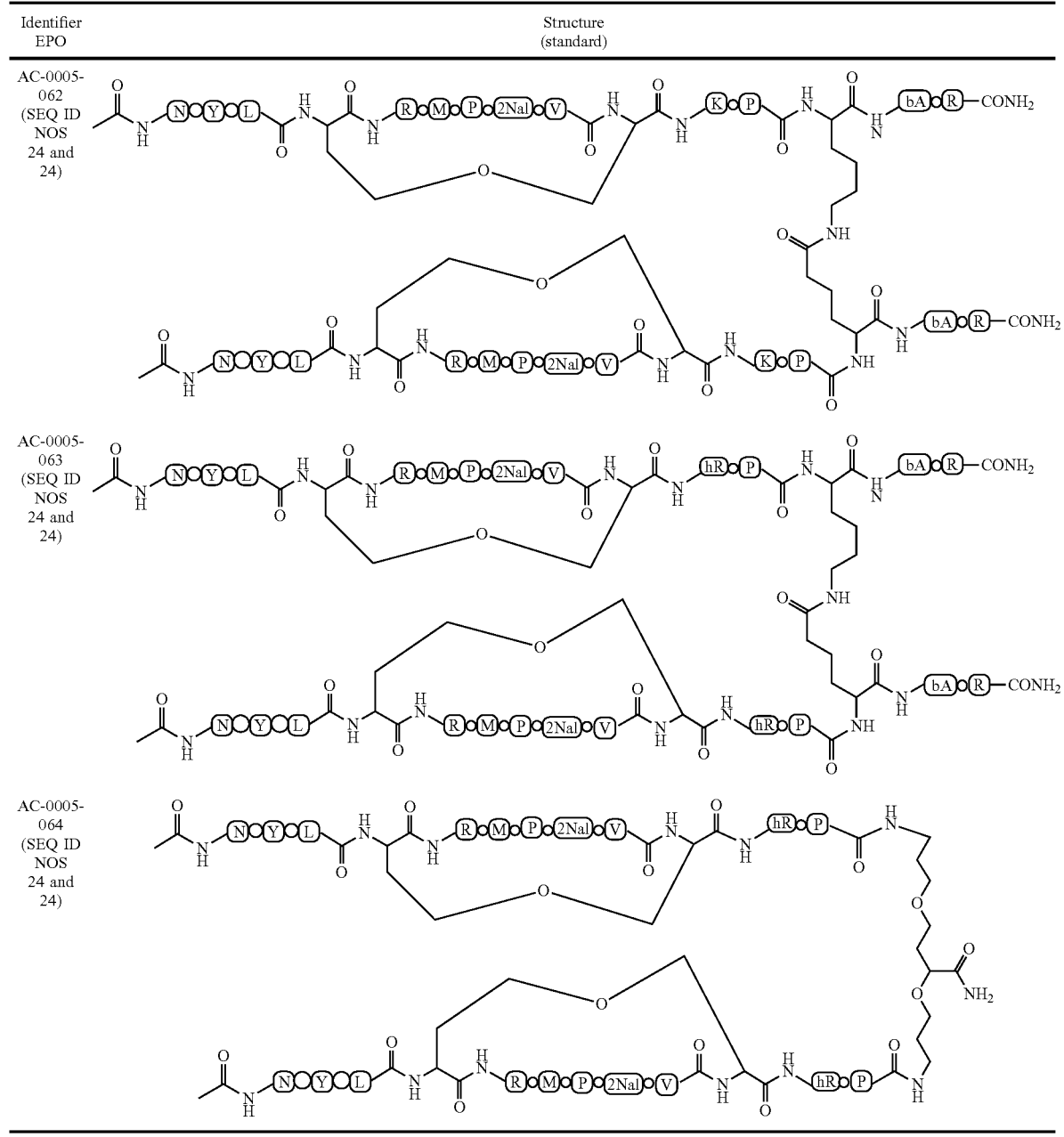

Example 3

A series of assays was carried out on several EPO mimetics that varied in their sequences at various locations. The results are as follows:

| Identifier | IC$_{50}$ | K$_I$ | N$_H$ |
|---|---|---|---|
| EPO | 0.163 nM | 0.0771 nM | 1.65 |
| AC-0005-026 | 0.0135 μM | 6.39 nM | 1.1 |
| AC-0005-051 | 0.0101 μM | 4.8 nM | 1.64 |
| AC-0005-052 | 0.0244 μM | 0.0116 μM | 1.52 |
| AC-0005-053 | 0.0192 μM | 9.09 nM | 1.86 |
| AC-0005-054 | 0.0651 μM | 0.0309 μM | 6.65 |
| AC-0005-055 | 0.011 μM | 5.23 nM | 1.38 |
| AC-0005-056 | 0.0235 μM | 0.0111 μM | 1.7 |
| AC-0005-057 | 0.0213 μM | 0.0101 μM | 1.84 |

Example 4

EPO mimetics were assayed for EPOR binding and resulted in the following IC$_{50}$ and K$_i$ values. (The last column expresses the K$_i$ relative to that of AC-0005-002):

| Identifier | IC$_{50}$ (nM) | K$_i$ (nM) | K$_i$ (AC-0005-002)/K$_i$ |
|---|---|---|---|
| Control: EPO | 0.24 | 0.11 | 3.5 × 10$^4$ |
| AC-0005-001 | 1298 | 615 | 6.3 |
| AC-0005-002 | 8167 | 3870 | 1 |
| AC-0005-003 | 119 | 56 | 69 |
| AC-0005-004 | 265 | 126 | 31 |
| AC-0005-005 | >10,000 | — | — |
| AC-0005-006 | >10,000 | — | — |
| AC-0005-007 | 4949 | 2350 | 1.7 |
| AC-0005-008 | >10,000 | — | — |

The affinity of compounds 001 to 008 for the EPOR was not optimal. Generally, smaller and/or more hydrophobic loop structures are preferred, the assay results for which are shown below. In addition, in the structural context of compound 007, the glutamine at position 14 appears suboptimal. Basic amino acid residues such as arginine, lysine or mimetics thereof are preferred at this position, as shown by the assay results below. (The last column expresses the K$_i$ relative to that of AC-0005-002):

| Identifier | IC$_{50}$ (nM) | K$_i$ (nM) | K$_i$ (AC-0005-002)/K$_i$ |
|---|---|---|---|
| Control 1: EPO | 0.54 | 0.26 | 1.5 × 10$^4$ |
| Control 2: AC-0005-003 | 171 | 81 | 48 |
| AC-0005-018 | 47 | 22 | 176 |
| AC-0005-019 | 57 | 27 | 143 |

Additional assays yielded the following results. (The last column expresses the K$_i$ relative to that of AC-0005-002):

| Identifier | IC$_{50}$ (nM) | K$_i$ (nM) | K$_i$ (AC-0005-002)/K$_i$ |
|---|---|---|---|
| Control 1: EPO | 0.14 | 0.064 | 50 |
| Control 2: AC-0005-003 | 164 | 78 | .041 |
| AC-0005-009 | 58660 | 27800 | 1.15 × 10$^{-4}$ |
| AC-0005-010 | 56420 | 26740 | 1.20 × 10$^{-4}$ |
| AC-0005-011 | 70470 | 33400 | 9.60 × 10$^{-5}$ |
| AC-0005-012 | 89780 | 42550 | 7.52 × 10$^{-5}$ |
| AC-0005-013 | 110300 | 52270 | 6.12 × 10$^{-5}$ |
| AC-0005-014 | 60400 | 28630 | 1.12 × 10$^{-4}$ |
| AC-0005-015 | 111900 | 53000 | 6.04 × 10$^{-5}$ |
| AC-0005-016 | 127700 | 60500 | 5.29 × 10$^{-5}$ |
| AC-0005-017 | 126800 | 60100 | 5.32 × 10$^{-5}$ |

Additional assays yielded the following results. (The last column expresses the K$_i$ relative to that of AC-0005-002):

| Identifier | IC$_{50}$ (nM) | K$_i$ (nM) | K$_i$ (AC-0005-002)/K$_i$ |
|---|---|---|---|
| Control 1: EPO | 0.22 | 0.1 | 3.9 × 10$^4$ |
| Control 2: AC-0005-018 | 70 | 33 | 117 |
| AC-0005-020 | 93 | 44 | 88 |
| AC-0005-021 | 25 | 12 | 323 |
| AC-0005-022 | 36 | 17 | 228 |
| AC-0005-023 | 35 | 17 | 228 |
| AC-0005-024 | 72 | 34 | 114 |
| AC-0005-025 | 48 | 23 | 168 |
| AC-0005-026 | 20 | 9 | 430 |
| AC-0005-027 | 63 | 30 | 129 |
| AC-0005-028 | 93 | 44 | 88 |

Additional assays yielded the following results. (The fourth column expresses the K$_i$ relative to that of AC-0005-002; the fifth column expresses the K$_i$ relative to that of EPO):

| Identifier | IC$_{50}$ (nM) | K$_i$ (nM) | K$_i$ (AC-0005-002)/K$_i$ | K$_i$/K$_i$(EPO) |
|---|---|---|---|---|
| Control 1: EPO | 0.16 | 0.08 | 3.9 × 10$^4$ | 1 |
| Control 2: AC-0005-026 | 12.4 | 5.9 | 656 | 74 |
| AC-0005-051 | 9.6 | 4.6 | 841 | 58 |
| AC-0005-052 | 24 | 11.4 | 339 | 143 |
| AC-0005-053 | 20 | 9.6 | 403 | 120 |
| AC-0005-054 | 33 | 15.5 | 250 | 194 |
| AC-0005-055 | 10.2 | 4.8 | 806 | 60 |
| AC-0005-056 | 24 | 11.2 | 346 | 140 |
| AC-0005-057 | 22 | 10.2 | 379 | 128 |

Additional assays yielded the following results. (The fourth column expresses the K$_i$ relative to that of AC-0005-002; the fifth column expresses the K$_i$ relative to that of EPO):

| Identifier | IC$_{50}$ (nM) | K$_i$ (nM) | K$_i$ (AC-0005-002)/K$_i$ | K$_i$/K$_i$(EPO) |
|---|---|---|---|---|
| Control 1: EPO | 0.13 | 0.06 | 3.9 × 10$^4$ | 1 |
| Control 2: AC-0005-026 | 9 | 4.3 | 900 | 72 |
| Control 3: AC-0005-055 | 12.6 | 6 | 645 | 100 |
| AC-0005-060 | 41.8 | 19.8 | 195 | 330 |
| AC-0005-061 | 58.5 | 27.7 | 140 | 462 |
| AC-0005-062 | 2.4 | 1.2 | 3336 | 19 |
| AC-0005-063 | 2.2 | 1 | 3720 | 17 |
| AC-0005-064 | 1.3 | 0.6 | 6450 | 10 |
| AC-0005-066/51 | 2.2 | 1.2 | 3250 | 20 |

While certain preferred and alternative embodiments of the present invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

All documents, patents and other literature referred to herein are incorporated by reference in their entirety.

The term "comprising" as used in the following claims is an open-ended transitional term that is intended to include additional elements not specifically recited in the claims. The term "consisting essentially of" as used in the following claims is a partially closed transitional phrase and is intended to include the recited elements plus any unspecified elements that do not materially affect the basic and novel characteristics of the claims. The term "consisting of" as used in the following claims is intended to indicate that the claims are restricted to the recited elements.

It should be noted that it is envisioned that any feature or element that is positively identified in this document may also be specifically excluded as a feature or element of an embodiment of the present invention as defined in the claims.

The invention claimed is:

1. An erythropoietin (EPO) mimetic comprising a first chain, a second chain and a linker wherein at least one of the first and second chains comprise:
   a. a loop consisting of five amino acid residues or mimetics thereof; and
   b. a bridge, wherein:
      i. the bridge comprises a series of between about three to about seven bonds, and
      ii. the bridge is covalently linked across the loop; and
   wherein the linker is covalently bound to each of the first and second chains at sequence positions of, independently, from between about residue 5 to about residue 18, and wherein at least two amino acid residues or mimetics thereof are independently selected from the group consisting of M, F, K, I, W, V, naphthylalanine and mimetics thereof.

2. The EPO mimetic of claim 1, wherein at least two of the amino acid residues or mimetics thereof are hydrophobic.

3. The EPO mimetic of claim 2, wherein the hydrophobic amino acid residues or mimetics thereof are selected from the group consisting of aliphatic amino acid residues, mimetics of aliphatic amino acid residues, aromatic amino acid residues, mimetics of amino acid residues, and combinations thereof.

4. The EPO mimetic of claim 1, further comprising at least one tail covalently bound to one of the first chain, the second chain or the linker.

5. The EPO mimetic of claim 4, wherein the tail comprises polyethylene glycol ("PEG"), polypropylene glycol, polyalkylene oxide, peptide, peptide mimetic, a fatty acid moiety, transporter moiety, a hydrogen, or moieties derived from amine, from carboxylic acid, from organic halide, from alcohol and from aldehyde.

6. The EPO mimetic of claim 5, wherein the tail comprises polyethylene glycol with a molecular weight of from between about 200 and about 20,000.

7. The EPO mimetic of claim 1, wherein the bridge comprises a series of between about four and about five bonds.

8. The EPO mimetic of claim 1, wherein the bridge is comprised of one or more selected from the group consisting of ether bonds, disulfide bonds, amide bonds, carbamate bonds, ester bonds, thioester bonds, polyether bonds, thioether bonds, phenolic ether bonds, amine bonds, sulfonamide bonds and carbon-carbon bonds.

9. The EPO mimetic of claim 8, wherein the bridge is comprised of ether bonds.

10. The EPO mimetic of claim 1, wherein the linker is an alkylene moiety selected from the group consisting of alkylene-O-alkylene$_m$, alkylene-N(R)C(=O)-alkylene$_m$, alkylene-C(=O)N(R)-alkylenem, alkylene-N(R)C(=O)O-alkylenem, alkylene-OC(=O)N(R)-alkylene$_m$, alkylene-OC(=O)-alkylene)$_m$, alkylene-C(=O)O-alkylene$_m$, alkylene-SC(=O)-alkylene$_m$, alkylene-C(=O)S-alkylene$_m$, alkylene-S-alkylene$_m$, alkylene-N(R)-alkylene$_m$, alkylene-N(R)SO$_2$-alkylene$_m$, alkylene-SO$_2$N(R)-alkylene$_m$, alkylene-C(=O)-alkylene$_m$ and combinations thereof, where R is hydrogen or a substituent and where m is selected from 1 to about 5.

11. The EPO mimetic of claim 1, further comprising at least one selected from the group consisting of linking moieties $L_1$, $L_2$, and $L_3$, a mid portion, an N-terminal end portion, a C-terminal end portion, a tail and combinations thereof.

12. The EPO mimetic of claim 11, wherein:
   a. the N-terminal end portion comprises the sequence of Ac-N-Y-L,
   b. the loop comprises the sequence of R-M-P-X-V (SEQ ID NO: 11),
   c. the C-terminal end portion comprises the sequence of X—P—R where X is homo-arginine, and
   d. the tail comprises at least one selected from the group consisting of polyethylene glycol, a fatty acid, an hSA binding peptide and combinations thereof.

13. A pharmaceutical composition comprising:
a. an EPO mimetic according to claim 1, and
b. a pharmaceutically acceptable excipient.

14. The pharmaceutical composition of claim 13, wherein the pharmaceutical composition is formulated for administration by inhalation, oral, parenteral, transdermal or transmucosal means.

15. The pharmaceutical composition of claim 14, wherein the pharmaceutical composition is formulated for administration by parenteral means.

16. A method for treating anemia, beta-thalassemia, acute blood loss, ischemia, boosting red blood count of a patient prior to surgery and combinations thereof, comprising the step of administering to a warm blooded animal in need thereof an EPO mimetic according to claim 1.

* * * * *